United States Patent [19]

Skibo et al.

[11] Patent Number: 5,246,955
[45] Date of Patent: Sep. 21, 1993

[54] ANTINEOPLASTIC COMPOUNDS AND METHODS OF USING SAME

[75] Inventors: Edward B. Skibo, Scottsdale; Imadul Islam, Tempe; David S. Alberts, Tucson, all of Ariz.

[73] Assignee: Research Corporation Technologies, Inc., Tucson, Ariz.

[21] Appl. No.: 835,620

[22] Filed: Feb. 13, 1992

Related U.S. Application Data

[63] Continuation of Ser. No. 502,334, Mar. 30, 1990, abandoned.

[51] Int. Cl.$^5$ .................. A01N 43/52; A61K 31/415
[52] U.S. Cl. .................................. 514/394; 548/302.4
[58] Field of Search ................ 514/394; 548/323, 325, 548/327

[56] References Cited

U.S. PATENT DOCUMENTS 5,015,742  5/1991  Skibo .................................. 548/323

FOREIGN PATENT DOCUMENTS 0449649  10/1991  European Pat. Off. .

OTHER PUBLICATIONS

Islam et al "Synthesis and Physical Studies of Azamitosene and Iminoazamitosene Reductive Alkylating Agents" J. Org. Chem. 1990, 55, 3195–3205.

*Primary Examiner*—Nathan M. Nutter
*Attorney, Agent, or Firm*—Richard R. Mybeck

[57] ABSTRACT

New cytotoxic quionones, designated amamitosenes and iminoazamitosenes are found to have significant activity against ovarian tumors, colon cancer, myecloma and the like neoplastic diseases.

Pharmaceutical preparations and therapeutic regimens utilizing azamitosenes and iminoazamitosenes and their pharmaceutically active derivatives are disclosed.

9 Claims, No Drawings

ANTINEOPLASTIC COMPOUNDS AND METHODS OF USING SAME

This invention was made with government support under grant No. 2 RO1CA 36876 awarded by the National Institute of Health. The U.S. government has certain rights in this invention.

This is a continuation of application Ser. No. 07/502,334 filed Mar. 30, 1990 and now abandoned.

INTRODUCTION

The present invention relates generally to new antineoplastic compounds and pharmaceutically acceptable derivatives thereof and the treatment of an afflicted host therewith. The essential moiety of the compound and derivatives hereof is 2,3-di hydro-1H pyrrolo [1,2-a] benzimidazole -5,8-diones (herein "azamitosenes") and the iminoquinone derivative thereof (herein "iminoazamitosenes")

BACKGROUND OF THE INVENTION

Mitomycins and the corresponding mitosene analogues are well-known examples of reductive alkylating quionones. The reductive alkylation process involves the formation of an alkylating quinone methide species upon reduction of the quinone and elimination of a leaving group. Since some tumor cells possess a low reduction potential environment, there is a great deal of interest in reductive alkylating quionones as selective antitumor agents. Thus, a wide range of mitomycin and mitosene derivatives have been prepared in an effort to optimize antitumor activity. All of these derivatives possess the indole ring nucleus, but with a variety of substituents.

Our efforts revealed that benzimidazole-based reductive alkylating agents are also capable of forming an alkylating quinone methide species. (See: Skibo, E. B., *J. Org. Chem* 1986, 51, 522). Altering the indole nucleus of mitosene to benzimidazole (azamitosene) therefore became important to terms of antitumor agent development.

The azamitosenes were found to possess potent in vitro anti-tumor activity against solid tumors such as colon and ovarian cancer. Some azamitosenes were found to provide results which were most favorable when compared to the clinically used drug, mitomycin C.

BRIEF SUMMARY OF THE INVENTION

The present invention relates to the discovery of a new and useful synthetic chemo therapeutic agent which can be formulated into useful pharmaceutical preparations having demonstratable and confirmed levels of anti-cancer activity when measured by generally accepted protocols in use at the United States National Cancer Institute. The principal substances referred to herein are the azamitosenes, the iminoazamitosenes, and the non-toxic pharmacologically active derivatives thereof.

The azamitosenes have the structural formula:

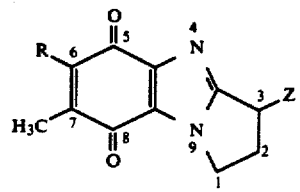

wheren:

| R is | Z is | |
|---|---|---|
| $H_3C{-}\overset{O}{\underset{\underset{H}{|}}{C}}{-}N$ | H | 1a |
| $H_3C{-}\overset{O}{\underset{\underset{H}{|}}{C}}{-}N$ | $\overset{O}{\underset{}{O{-}C{-}CH_3}}$ | 1b |
| ⌐N | $\overset{O}{\underset{}{O{-}C{-}CH_3}}$ | 1c |
| ⌐N | $\overset{O}{\underset{}{O{-}C{-}NH_2}}$ | 1d |

The iminoazamitosenes have the structural formula:

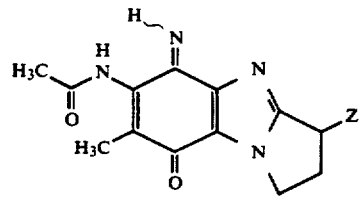

wherein:

| Z is | |
|---|---|
| H | 2a |
| $\overset{O}{\underset{}{O{-}C{-}CH_3}}$ | 2b |

Accordingly, a principal object of the present invention is to provide new agents useful for retardation or remission of one or more types of cancer including ovarian cancer, colon cancer, myeloma and the like.

These and still further objects, as shall hereinafter appear, are readily fulfilled by the present invention in a remarkably unexpected manner as will be readily discerned from the following detailed description of exemplary embodiments thereof.

DESCRIPTION OF PREFERRED EMBODIMENT

Azamitosene and Iminoazamitosene Synthesis. Preparation of the azamitosene ring system (2,3-dihydro-1H-pyrrolo[1,2-a]benzimidazole) was completed by using the Lewis acid catalyzed cyclization of an ortho-nitropyrrolidinobenzene derivative (e.g., compound 3→4 in Scheme 1 and compound 17→19 in Scheme 3) and by the oxidative cyclization of a diacetamido pyrrolidinobenzene derivative (e.g., 10→11 in scheme 2 and 18→20 in scheme 3). (See: Grantham et al, *J. Chem. Soc.* (C). 1969, 70; Nair et al, *J. Am. Chem. Soc.*, 1961, 83, 3518). The first reaction was employed to prepare azamitosenes having a leaving group at the 3- position and the second reaction was employed to prepare the 3-unsubstituted derivatives. Quinone and iminoquinone elaboration was carried out by Fremy oxidation of aromatic amine derivatives in pH~3 and in pH=7.0 aqueous buffers, respectively.

The synthesis of the antitumor agents 1c,d is shown in Scheme 1. The pyrrolo[1,2a]benzimidazole derivative 4 was brominated at the 6-position so as to direct nitration to the 5-position in the next step (5→6). Catalytic reduction of 6 resulted in both amine reduction and hydrogenolysis of the bromo substituent to afford 7c. The acetate leaving group of 6 was converted to carbamate (6→8) followed by catalytic reduction to afford 7d. Finally, Fremy oxidation of 7c,d to 9c,d and then reductive addition of ethyleneimine in the presence of air afforded 1c,d.

The synthesis of the antitumor agent 16 in shown is Scheme 2. The pyrrolo [1,2-a] benzimidazole derivative 11 was subject to the bromination, nitration, and reduction sequence to afford 14. Fremy oxidation of 14 and then reductive addition of ethylenemine in the presence of air afforded 16.

The synthesis of the stabilized iminoquinones syn-2a,b and anti-2a,b is shown in Scheme 3. Fremy oxidation of 23a,b in pH 7.0 phosphate buffer afforded a syn/anti mixture of iminoquinone isomers, which can be separated by fractional crystallization as described hereinafter in greater detail. Fremy oxidation of these same starting materials in pH~3 buffer afforded the quionones 1a,b.

Structural assignments of the iminoquinone isomers were possible using $^1$H NMR chemical shifts obtained in dimethyl sulfoxide-d$_6$ (DMSO d$_6$). The syn/anti isomers also possess different IR and UV-visible spectra. Intramolecular proton transfer only in the syn isomer is likely responsible for all of the observed spectral differences.

The $^1$H NMR chemical shifts (dimethyl sulfoxide-d$_6$) of the acetamido methyl and 7-methyl groups of syn 2a are shifted upfield relative to those of anti 2a. This observation is consistent with the formation of a delocalized negative charge at the centers bearing the methyl groups in the syn isomer upon intramolecular proton transfer. In contrast, the imino-nitrogen lone pair of anti 2a is anti to the amide proton and a zwitterion cannot form. Nuclear Overhauser effects (NOE) are also consistent with the assigned structures in Scheme 4. In the zwitterionic form, the iminium proton at $\delta$9.19 shows NOE interactions with both the acetamido and 7 methyls while the $\delta$6.24 iminium proton does not. On the other hand, both nitrogen-substituted protons of anti 2a show NOE interaction with these methyls. The NOE interactions for the $\delta$9.59 proton with the methyl groups are much greater than those observed for the 11.42 proton, which led to the assignments shown in Scheme 4 below. These assignments are consistent with literature values of imino protons chemical shifts ($\delta$=11.2) and with the acetamido nitrogen proton chemical shifts ($\delta$7.5-9.3) reported herein.

The IR spectra (KBr pellet) of syn and anti 2a also supports intramolecular proton transfer in the former compound The quinone carbonyl stretching frequency of anti 2a (1683 cm$^{-1}$) is greater than that of syn 2a (1652 cm$^{-1}$) due to the decrease in carbonyl bond order in the zwitterion.

SCHEME 1

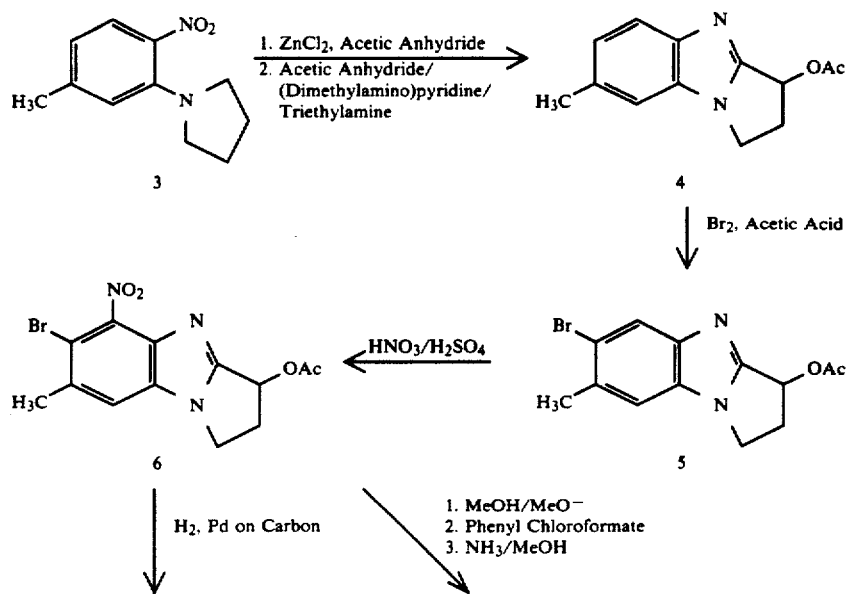

SCHEME 1
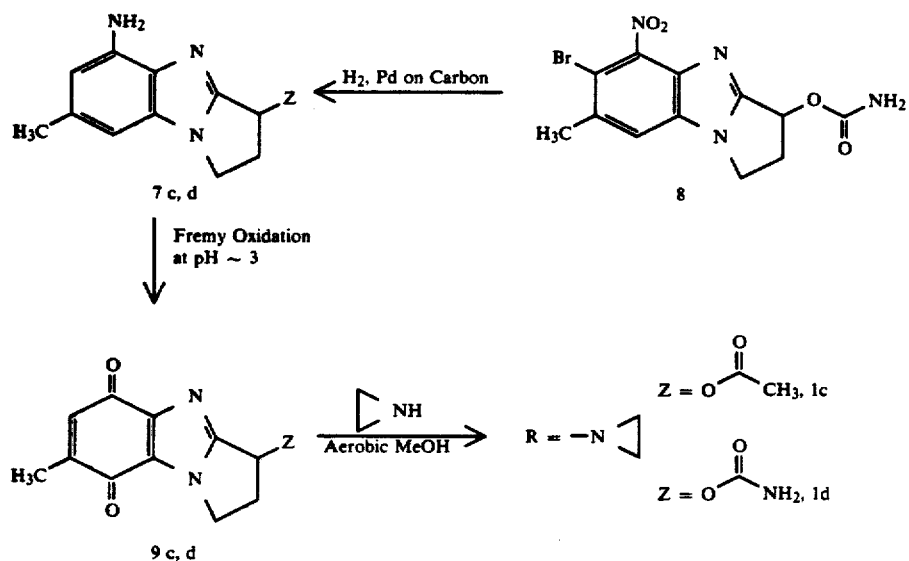
SCHEME 2
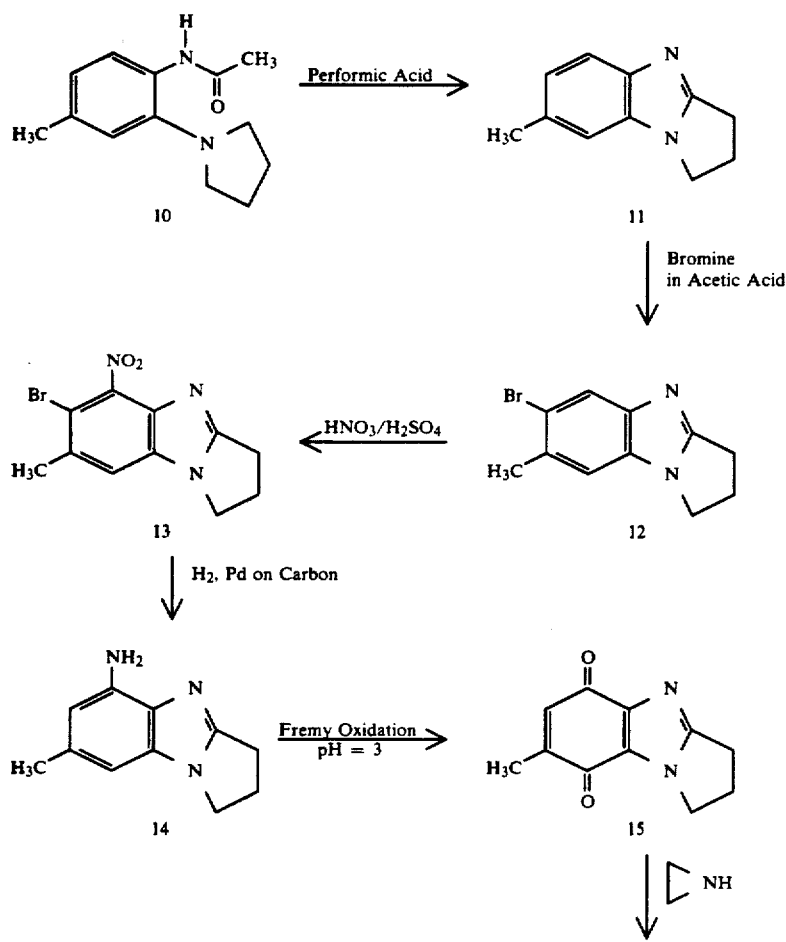

SCHEME 2
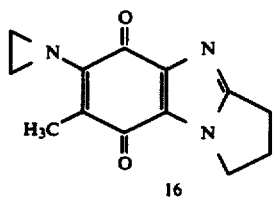
SCHEME 3
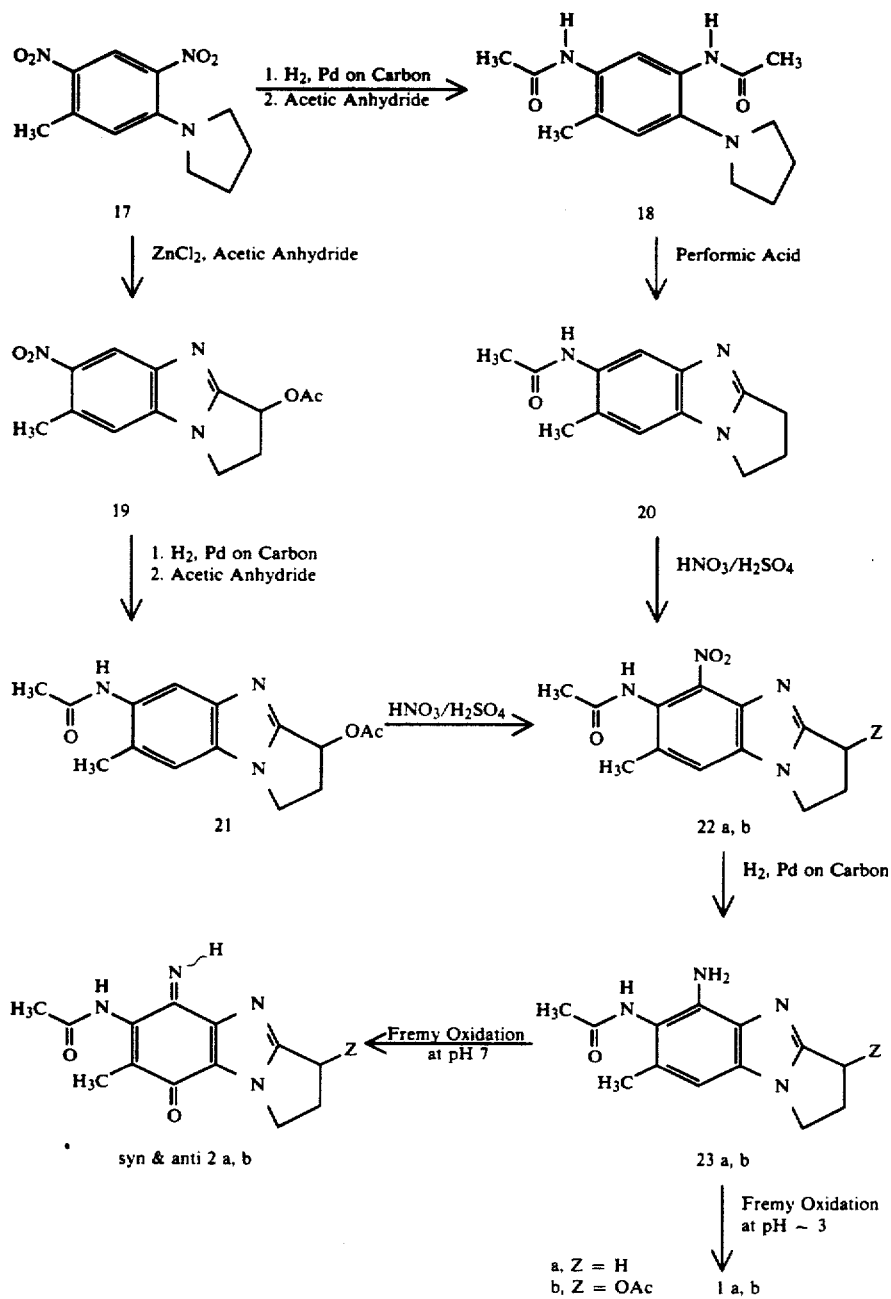

SCHEME 4

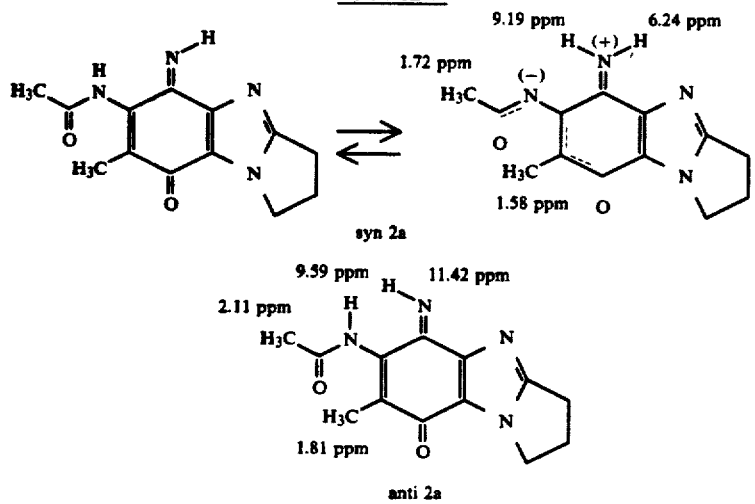

Experimental Section

All analytically pure compounds were dried under high vacuum at room temperature or in a drying pistol heated wtih refluxing methanol. Compounds susceptible to decomposition (1c,d, 2, ) were not heated above room temperature. Some of the compounds still contained water of crystallization that was determined from the elemental analyses found. Experimental nitrogen percentages for 1c,d, and syn 2a deviated from theoretical percentages b>0.5%. Repeat nitrogen analyses often showed a wide variation in percentage values; we believe this is due to incomplete combustion. $^1$H NMR and $^{13}$C NMR data and mass spectra (both the parent ion and fragmentation pattern) supported the assigned structures and TLC indicates these compounds are pure. No elemental analyses were obtained for anti 2a,b, 7c,d, 2,; spectral data support the assigned structures and these compounds can be converted to well-characterized compounds.

Uncorrected melting and decomposition points were determined with a Mel-Temp apparatus. All TLC was run with Merck silica gel 60 ($F_{254}$) plates, employing a variety of solvents. IR spectra were taken as KBr pellets or thin films; the strongest IR absorbances are reported. $^1$H and $^{13}$C NMR spectra were obtained on a Bruker AM-400 spectrometer and chemical shifts are reported relative to TMS.

Synthesis and Physical Properties of new compounds are provided below:

3-(N-pyrrolidino)-4-nitrotoluene (3). A mixture of 8.64 g (40 mmol) of 3-bromo-4-nitrotoluene and 8.5 g (120 mmol) of pyrrolidine was heated at reflux for 3 hours. The cooled reaction mixture was poured over 200 g of cracked ice and the resulting mixture extracted 2× with 200 mL portions of chloroform. The dried extracts (sodium sulfate) were concentrated to an oily residue, which was placed on a silica gel flash column. The product was eluted with hexane/chloroform (50:50). Evaporation of the eluant afforded an orange oil, which slowly solidified upon chilling in a refrigerator: yield 7.8 g (94%); mp 42° C.; TLC (CHCl3), $R_f$=0.46;IR (film on NaCl) 1612, 1569, 1500, 1465, 1447, 1430, 1360, 1356, 1274, 600 cm$^{-1}$; NMR (CDCl3)δ6.52 and 7.66 2 H, ABX, $J_{ortho}$=8.24 Hz, $J_{meta}$=1.3 Hz, $J_{para}$~0 Hz, C(5) and C(6) aromatic protons, respectively), 6.69 (1 H, br s, C(2) aromatic proton), 3.20 (4 H, m, pyrrolidine methylenes adjacent to N), 2.34 (3 H, s, methyl), 1.97 (4 H, m, other pyrrolidine methylenes); mass spectrum (EI mode), m/z 206 (P+) Anal. Calcd for $C_{11}H_{14}N_2O_2$: C, 64.05; H, 6.84; N, 13.58. Found: C, 63.49; H, 6.73; N, 13.32.

7-Methyl-2,3-dihydro-1H-pyrrolo[1,2-a]benzimidazole-3-Acetate (4). A mixture consisting of 2.06 g (10 mmol) of 3, 1.36 g (10 mmol) of anhydrous $ZnCl_2$, and 10 mL of acetic anhydride was stirred at 100°-110° C. for 5 hours( or until 3 was no longer seen by TLC). The reaction mixture was poured into 10 mL of water and the black oil which formed was separated and evaporated to a small volume. The residue was combined with 20 mL of concentrated HCl and warmed to 80° C. for 5 min. Hydrogen sulfide gas was then passed into the HCl solution for 5 min followed by addition of NaOH until the pH 6.5-7.0. Extraction of the above mixture with 3×50 mL portions of chloroform, drying the extracts (sodium sulfate), and chromatography on silica gel (column prepared with chloroform and the product eluted with chloroform/methanol [95:5]) afforded the 3-hydroxy derivative of 4 as a white powder: 1.00 g (52%) yield; mp 212° C.; TLC (chloroform/methanol [90:10]), $R_f$=0.52; IR (KBr pellet) 3135, 2861, 1524, 1445, 1350 1322, 1298, 1290, 1092, 816 cm$^{-1}$; $^1$H NMR (dimethyl sulfoxide-d6) δ7.46 and 6.98 (2 H, ABX system, $J_{ortho}$=8.2 Hz, $J_{meta}$=1.20 Hz; $J_{para}$~0 Hz, C(5) and C(6) protons, respectively), 7.26 (1 H, br s, C(8) proton), 5.78 (1 H, d, J=6.0 Hz, 3-hydroxyl proton), 5.05 (1 H, M, C(3) H, m, C(3) proton), 4.15 and 3.99 (2 H, 2×m, C(1) diastereomeric methylene), 2.88 and 2.36 (2 H, 2×m, C(2) diastereomeric methylene), 2.40 (3H, s, 7-methyl); mass spectrum (EI mode) m/z 188 (P+) 171 (p+- OH). Anal Calcd for $C_{11}H_{12}N_2O$: C, 70.21; H, 6.38; N, 14.89. Found: C, 69.84; H, 6.33; N, 14.82.

Acetylation of the alcohol obtained above was carried out by stirring a mixture consisting of 376 mg (2 mmol) of the alcohol, 224 mg (2.07 mmol) of acetic anhydride, 122 mg (1 mmol) of (dimethylamino)pyridine, 220 mg (2.2 mmol) of triethylamine, and 20 mL of methylene chloride for 30 min at room temperature. The reaction mixture was then washed with water (3×25 mL) and dried over sodium sulfate. Evaporation of mixture to an oil and trituration with chloroform- /hexane afforded 4 as a white solid; 391 mg (85%) yield; mp 154° C.; TLC (chloroform/methanol [90:10]), $R_f=0.76$; IR(KBr pellet)1747, 1537, 1427, 1372, 1291, 1269, 1251, 1224, 1053, 808 cm$^{-1}$; $^1$H NMR (dimethyl sulfoxide-d$_6$)δ7.50 and 7.04 ( 2 H, ABX system, J$_{ortho}$=8.3 Hz, J$_{meta}$=1.3 Hz, J$_{para}$~0 Hz, C(5) and C(6) aromatic protons, respectively), 7.26 (1 H, br s, C(8) aromatic proton), 6.10 (1 H, dd, J=7.6 Hz, J=3.3 Hz, C(3) proton), 4.22 and 4.12 (2 H, 2×m, C(1) diastereomeric methylene), 3.10 and 2.56 (2 H, 2×m, C(2) diastereomeric methylene, 2.43 (3 H, s, 7-methyl), 2.07 (3 H, s, acetate methyl); mass spectrum (EI mode) m/z 230 (P+187 (P+-acetyl). Anal. Calcd for C$_{13}$H$_{14}$N$_2$O$_2$: 67.88; H, 6.12; N, 12.16. Found: C, 67.26; H, 5.99; N, 11.94.

6-Bromo-7-methyl-2,3-dihydro-1H -pyrrolo[[1,2-a]benzimidazole-3-Acetate (5). To a solution of 500 mg (2.17 mmol) of 4 in 10 mL of glacial acetic acid, heated at 100° C., was added 3 mL of 0.72 M bromine in glacial acetic acid. After the addition, the reaction mixture was heated at 100°=110° C. for 4 hours. The cooled reaction mixture was diluted with 20 mL of water and then neutralized to pH 6.5 with aqueous sodium bicarbonate. The product crystallized from the solution as white crystals; yield upon drying the collected solid was 510 mg (75%). Recrystallization from chloroform/hexane afforded analytically pure material: dec pt 191° C.; TLC (chloroform/methanol [80:20], $R_f=0.64$; IR (KBr pellet) 1748, 1531, 1455, 1424, 1371, 1288, 1249, 1082, 1051, 851 cm$^{-1}$; $^1$H NMR (dimethyl sulfoxide-d$_6$)δ7.86 and 7.58 ( 2 H, 2×s, aromatic protons), 6.11 ( 1 H, dd, J=7.6 Hz, J=3.2 Hz, C(3) proton coupled to C(2) methylene) 4.23 and 4.12 (2 H, 2×m, C(1) diastereomeric methylene) 3.12 and 2.52 (2 H, 2×m, C(2) diastereomeric methylene), 2.49 (3 H, s, 7-methyl), 2.07 3 H, s, acetate methyl); mass spectrum (EI mode) m/z 308 and 310 (P+, Br and P+, $^{81}$Br), 265 and 267 (P+- acetyl) 249 and 251 (P+- acetic acid). Anal. Calcd for C$_{13}$H$_{13}$BrN$_2$O$_2$ 0.25.H$_2$O: C, 49.76; H, 4.25; N, 8.92. Found: C, 50.00; H, 4.20; N, 8.85.

6-Bromo-7-methyl-5-nitro-2,3-dihydro-1H-pyrrolo [1,2-a]benzimidazole-3-Acetate (6). A solution of 500 mg 1.61 mmol) of 5 in 10 mL of a 9:1 mixture of fuming nitric acid and concentrated sulfuric acid was stirred in an ice bath for 10 min. The completed reaction was poured over cracked ice and the pH of the resulting solution adjusted to pH 6.5 with aqueous sodium bicarbonate. Extraction of this solution with 3×50 mL of chloroform, drying the extracts (sodium sulfate), and then concentration afforded a yellow oil. Dissolution of this oil in a small volume of chloroform and addition of hexane resulted crystallization of 6: 411 mg (71%) yield; dec pt 185° C.; TLC (chloroform/methanol [80:20]), $R_f=0.73$; IR (KBr pellet) 1747, 1539, 1488, 1442, 1374, 1350, 1305, 1232, 1089, 1044 cm$^{-1}$; $^1$H NMR (dimethyl sulfoxide -d$_6$) δ7.90 (1 H, s, aromatic), 6.15 (1 H, dd, J=7.7 Hz, J =3.2 Hz, C(3) proton coupled with C(2) methylene), 4.33 and 4.20 (2 H, 2×m, C(1) diastereomeric methylene), 3.15 and 2.60 (2 H, 2×m, C(2) diastereomeric methylene), 2.55 (3 H, s, 7-methyl), 2.09 (3 H, s, acetate methyl); mass spectrum (EI mode) m/z 353 and 355 (P+, $^{79}$Br and P+, $^{81}$Br), 310 and 312 (p+- acetyl), 293 and 295 (P+-acetic acid). Anal. Calcd for C$_{13}$H$_{12}$BrN$_3$O$_4$: C, 44.07; H, 3.41; N, 11.86. Found: C, 44.16; H, 3.27; N, 11.59. 6-Bromo-7-methyl-5-nitro-2,3-dihydro-1H-pyrrolo 1,2a]benzimidazole-3-Carbamate (8). The conversion of 6 to 8 was carried out by the three-step process described below.

Deacetylation was carried out by suspending 200 mg (0.56 mmol) of 6 in 25 mL of methanol and then adding 31 mg of sodium methoxide. The reaction was stirred for 30 min at room temperature and the crystallized alcohol derivative filtered off; 142 mg (81%) yield. Recrystallization was carried out by dissolving the product in 15 mL of methanol-chloroform (1:4) and then adding a small amount of hexane followed by chilling: dec pt 255° C.; TLC (chloroform/methanol [90:10], ), $R_f=0.4$; (KBr pellet) 3200, 1545, 1516, 1438, 1381, 1372, 1345, 1299, 1101 cm$^{-1}$; $^1$H NMR (dimethyl sulfoxide-d$_6$)δ7.83 (1H, s, aromatic), 6.03 H, d, J=5.6 Hz, 3 -hydroxyl), 5.13 ($^1$H, m, C(3) proton), 4.27 and 4.09 (2 H, 2×m, C(1)-diastereomeric protons), 2.94 and 2.41 (2 H, 2×m, C(2)-diastereomeric protons), 2.53 (3 H, s, 7-methyl); mass spectrum (EI mode) m/z 311 and 313 (P+, $^{79}$Br and P+, $^{81}$Br). Anal. Calcd for C$_{11}$H$_{10}$BrN$_3$O$_3$: C, 42.31; H, 3.22; N, 13.46. Found: C, 42.44; H, 3.13; N, 13.34.

The phenyl carbonate derivative of the alcohol was prepared as described below. To a solution of the alcohol (400 mg, 1.27 mmol) in 20 mL of pyridine, chilled to 0° C., was added 400 μl of phenyl chloroformate. The reaction was stirred at 0° C. for 15 min and then at room temperature for 1 hour. The completed reaction was diluted with 150 mL of ethyl acetate and the resulting mixture extracted 3×with 50 mL of 20% acetic acid and then 2×with 50 mL of water. Drying of the extracts (sodium sulfate) and concentration afforded the carbonate as a light yellow solid; yield 450 mg (81%). Recrystallization was 11.59. carried out from chloroform/hexane; mp 172°–175° C.; TLC (chloroform/methanol [90:10], $R_f=0.64$; IR (KBr pellet) 1765, 1538, 1350, 1293, 1249, 1201, 1184, 1084, 946, 777 cm$^{-1}$; $^1$H NMR (dimethyl sulfoxide-d$_6$) δ7.94 (1 H, s, aromatic), 7.46 and 7.31 (5 H, 2×x m, 11.59. phenyl), 6.22 (1 H, dd, J=7.5 Hz, J=3.6 Hz, C(3) proton), 4.39 and 4.26 (2 H, 2×m, C(1) diastereomeric methylene), 3.24 and 2.85 (2 H, 2×m, C(2) diastereomeric methylene), 2.56 (3 H, s, 7-methyl); mass spectrum (EI mode) m/z 431 and 433 (P+, $^{79}$Br and P+, $^{81}$Br), 294 and 296 (P+- Ph-O-CO$_2$). Anal. Calcd for C$_{18}$H$_{14}$BrN$_3$O$_5$.0.25 H$_2$O: C, 49.49; H, 3.28; N, 9.61. Found: C, 49.62; H, 3.17; N, 9.51.

The preparation of the carbamate 8 was carried out by treatment of the carbonate derivative with ammonia. To 30 mL of anhydrous ammonia at −76° C. was added a solution of the carbonate, 211 mg (0.48 mmol), in 30 mL of dry dichloromethane. The solution was stirred at −76° C. for 30 min and allowed to come to room temperature over a 3 hour period. The solvent was evaporated and the solid residue recrystallized from chloroform/hexane to afford yellow crystals of 8: dec pt 236° C.; TLC (chloroform/methanol [90:10]), $R_f=0.4$; IR (KBr pellet) 3372, 1715, 1533, 1416, 1400, 1378, 1370, 1335, 1300, 1094 cm$^{-1}$; $^1$H NMR (dimethyl sulfoxide-d$_6$) δ7.89 (1 H, s, aromatic), 6.82 and 6.73 (2 H, 2×br s, amide protons), 6.00 (1 H, dd, J=7.5 Hz, J=3.8 Hz, C(3) proton) 4.30 and 4.80 (2 H, 2×m, C(1) diastereomeric methylene) 3.13 and 2.55 (2 H, 2×m, C(2) diastereomeric methylene), 2.54 (3 H, s, 7-methyl); mass spectrum (EI mode) m/z 354 and 356 (P+, $^{79}$Br and p+, $^{81}$Br), 312 and 313 (P+- 0=C=N−H), 293 and 295 (P+- carbamic acid). Anal. Calcd for C$_{12}$H$_{14}$BrN$_4$O$_2$: C, 40.58; H, 3.11; N, 15.77. Found: C, 40.61; H, 3.13; N, 15.41.

5-Amino-7-methyl-2,3-dihydro-1H-pyrrolo[1,2-a]benzimidazole-3-Acetate and 3-Carbamate (7c and 7d). A suspension of 6 or 8 in 100 mL of methanol containing 60 mg 5% Pd on charcoal was shaken under 50 psi H$_2$ for 6 hours. The reaction was filtered through Celite and the filter cake washed with methanol. Acidification of the filtrate with a few drops of 1 N HCl and evaporation in vacuo afforded the dihydrochloride salt of the amine. Recrystallization was carried out from ethyl acetate/methanol.

Reduction of 6 afforded an 80% yield of the dihydrochloride salt of 7c: dec pt 250° C.; TLC (chloroform-/methanol [90:10]), R$_f$=0.67; IR (KBr pellet) 3384, 3313, 3205, 2853, 2836, 2752, 1750, 1643, 1494, 1218 cm$^{-1}$; $^1$H NMR (dimethyl sulfoxide-d$_6$) δ6.99 (1 H, s, C(8) proton), 6.73 (1 H, s, C(6) proton),6.25 (1 H, dd, J=7.9 Hz, J=3.7 Hz, C(3) proton, 4.40 and 4.26 (2 H, 2×m, C(1) diastereomeric methylene) 3.19 and 2.70 (2 H, 2×m, C(2) diastereomeric methylene), 2.38 (3 H, s, 7-methyl), 2.12 (3 H, s, acetate methyl); mass spectrum (EI mode) m/z 245 (P+of base), 202 (P+- acetyl, 186 (P+-acetamide).

Reduction of 8 afforded an 87% yield of the dihydrochloride salt of 7d: dec pt 245° C.; TLC (chloroform-/methanol [80:20]), R$_f$=0.48; IR (KBr pellet) 3315, 3270, 3200, 3146, 3041, 1736, 1402, 1370, 1318 cm$^{-1}$,; $^1$H NMR (dimethyl sulfoxide-d$_6$)δ7.04 and 6.93 (2 H, 2×br s, amide protons), 6.88 (1 H, s, C(8) proton), 6.64 (1 H, s, C(6) proton), 6.12 (1 H, dd, J=8.0 Hz, J=3.9 Hz, C(3) proton), 4.39 and 4.24 (2 H, 2×m, C(2) diastereomeric methylene), 3.22 and 2.65 (2 H, 2×m, C(2) diastereomeric methylene) 2.36 (2 H, s, 7-methyl); mass spectrum (EI mode) m/z 246 (P+), 202 (P+-O=C=NH$_2$), 185 (P+- carbamic acid).

7-Methyl-2,3-dihydro-1H-pyrrolo[1,2-a]benzimidazole-5,8-dione-3-Acetate and 3-Carbamate (9c and 9d). To a suspension of 0.35 mmol 7c or 7d in 10 mL of water containing 80 mg of monobasic potassium phosphate was added a solution of 500 mg of Fremy's salt in 50 mL of water containing 200 mg of monobasic potassium phosphate. The reaction mixture was stirred at room temperature for 1.5 hours and then extracted 5× with 20 mL of chloroform. The dried extracts (sodium sulfate) were concentrated to an oil and then flash chromatographed employing silica gel with acetone (9d) or chloroform (9c) as eluant. The product was recrystallized from acetone/hexane.

Oxidation of 7c afforded a 54% yield of 9c: mp 132°-135° C.; TLC (acetone), R$_f$=0.67; IR (KBr pellet) 1746, 1739, 1673, 1653, 1610, 1510, 1372, 1329, 1235, 1154 cm$^{-1}$; $^1$H NMR (CDCl$_3$)δ6.54 (1 H, q, J=1.2 Hz, C(6) proton), 6.09 (1 H, dd, J=7.6 Hz, J=2.9 Hz, C(3) proton), 4.40 and 4.31 (2 H, 2×m, C(1) diastereomeric methylene), 3.18 and 2.66 (2 H, 2×m, C(2) diastereomeric methylene) 2.11 (3 H, d, J=1.2 Hz, 7-methyl), 2.10 (3 H, s, acetate methyl); mass spectrum (EI mode) m/z 260 (P+), 217 (P+-acetyl), 200 (P+- acetic acid). Anal. Calcd for C$_{13}$H$_{12}$N$_2$O$_4$: C, 59.99; H, 4.64; N, 10.76. Found: C, 59.55; H, 4.70; N, 10.53.

Oxidation of 7d afforded a 58% yield of 9d: dec pt 201° C.; TLC (acetone), R$_f$=0.53; IR (KBr pellet) 3411, 1741, 1735, 1727, 1654, 1610, 1330, 1168, 1155, 1147 cm$^{-1}$;$^1$H 1H NMR (CDCl$_3$)δ6.54 (1 H, q, J=~1 Hz, C(6) proton), 6.01 (1 H, dd, J=7.6 Hz, J=3.3 Hz, C(3) proton), 4.70 (2 H, br s, amide protons), 4.40 and 4.29 (2 H, 2×m, C(1) diastereomeric methylene) 3.17 and 2.73 (2 H, 2×m, C(2) diastereomeric methylene), 2.10 (3 H, d, J~1 Hz, 7-methyl); mass spectrum (EI mode) m/z 261 (P+), 217 (P+- O=C-NH$_2$), 201 (P+- carbamate). Anal. Calcd for C$_{12}$H$_{11}$N$_3$O$_4$: C, 55.17; H, 4.24; N, 16.08. Found: C, 55.65; H, 4.28; N, 16.26.

6-(N-aziridinyl)-7-methyl-2,3-dihydro-1H-pyrrolo 1,2-a]benzimidazole-5,8-dione-3-Acetate (1C). To a solution of 52 mg (0.2 mmol) of 9c in 2 mL of methanol, chilled at 0° C., was added 0.5 mL of ethyleneimine. After stirring at 0° C. for 30 min, the reaction was stirred at room temperature for 1 hour. The solvent was then removed in vacuo and the brick-red residue flash chromatographed on silica gel using chloroform as eluant. The purified product was recrystallized from methylene chloride/hexane: 25 mg (42%) yield; mp 125°-127° C.; TLC (acetone), R$_f$=0.65; IR (K8r pellet) 1746 1679, 1636, 1518, 1378, 1341, 1314, 1230, 1141, 1035 cm$^{-1}$; $^1$H NMR (CDCl$_3$)δ6.05 (1 H, dd, J=7.5 Hz, J=3 Hz, C(3) proton), 4.29 (2 H, m, C(1) diastereomeric methylene), 3.13 and 2.62 (2 H, 2×m, C(2) diastereomeric methylene), 2.36 (4 H, s, aziridine protons), 2.09 (3 H, s, 7-methyl), 2.07 (3 H, s, acetate methyl); 13C NMR (CDCl$_3$)δ178.0, 176.7, 169.9, 155.9, 153.1, 144.5, 130.3, 124.6, 66.4, 43.6, 35.0, 29.4, 20.8, 9.5 cps; mass spectrum EI mode) m/z 301 (P+- methyl), 258 (P+-acetyl). Anal. Calcd for C$_{15}$H$_{15}$N$_3$O$_4$: or C, 59.79; H, 5.01; N, 13.94. Found: C, 59.65; H, 5.06; N, 12.96 to 13.28.

6-Aziridinyl-7-methyl-2,3-dihydro-1H-pyrrolo [1,2-a]benzimidazole-5,8-dione-3-Carbamate (1d). A solution of 26 mg (0.1 mmol) of 9d in 7 mL of methanol was combined with 0.25 mL of ethyleneimine and the mixture stirred at room temperature for 1.5 hours. The solvent was evaporated in vacuo and the red residue flash chromatographed on silica gel using acetone as eluant. The product was recrystallized from acetone/-hexane 15 mg (50% yield; dec pt 1185° C.; oC; TLC (acetone), R$_f$=0.52; IR (KBr pellet), 3444, 3364, 1727, 1653, 1325, 1311 cm$^{-1}$; $^1$H NMR (CDCl$_3$)δ5.98 (1 H, dd, J=7.5 Hz, J=3 Hz, C(3) proton), 4.68 (2 H, br s, amide protons), 4.36 and 4.28 (2 H, 2×m, C(1) diastereomeric methylene), 3.15 and 2.71 (2 H, 2×m, C(2) diastereomeric methylene), 2.36 (4 H, s, aziridinyl protons), 2.08 (3 H, s, 7-methyl); 13C NMR (CDCl$_3$)δ178.0, 176.7 156.0, 155.3, 153.0, 144.4, 130.3, 124.5, 67.2, 43.6, 35.1, 29.4, 9.5 cps; mass spectrum (EI mode) m/z 302 (P+), 259 (P+- 0=C=N-H). Anal. Calcd for C$_{14}$H$_{14}$N$_4$O$_4$. 0.5 H$_2$O: C, 54.01; H, 4.85; N, 17.99. Found: C, 54.03; H, 4.58; N, 16.81-16.70.

4-Acetamido-5-(N-pyrrolidino)toluene (10). A mixture consisting of 6.2 g (30.09 mmol) of 3-(N-pyrrolidino)-4-nitrotoluene, 500 mg of 5% Pd/C, and 250 mL of methanol was shaken under 50 psi for 4 hour. The completed reaction was filtered through Celite into a flask containing 10 mL of acetic acid. The filtrate was then evaporated in vacuo to an acetic acid/amine mixture, to which was added 10 mL of acetic anhydride. The mixture was stirred at room temperature and then diluted with 300 mL of diethyl ether. Pure product crystallized from the mixture after sonication and then chilling overnight, 5.46 g (83%) yield. Recrystallization was carried out from chloroform/hexane: m.p. 92°-94° C.; TLC (Chloroform) R$_f$=0.75; IR(KBr pellet) 1655, 1644, 1605, 1534, 1509, 1489, 1418, 1373, 1355, 1329 cm$^{-1}$; $^1$H NMR (dimethyl sulfoxide-d$_6$)δ9.03 (1 H, s, amide proton), 7.05 and 6.57 (2 H, ABX, J$_{ortho}$=7.8 Hz, J$_{meta}$=0 Hz, J$_{para}$=0 Hz, C(5) and C(6) protons), 6.62 (1H, s, C(2), proton), 3.13 (4 H, m, pyrrolidine methylenes adjacent to N), 2.21 (3H, s, methyl), 1.98 (3H, S, acetamide methyl), 1.84 (4 H, m, other pyrrolidine methylenes); mass spectrum (EI mode) m/z 218 (P+), 175 (P+- acetyl). Anal. Calcd for C$_{13}$H$_{18}$N$_2$O: C, 71.52; H, 8.31; N, 12.83. Found: C, 71.28; H, 8.19; N, 12.95.

7-Methyl-2,3-dihydro-1H-pyrrolo[1,2-a]benzimidazole (1). A mixture consisting of 1.0 g (4.58 mmol) of 10, 3 mL of 96% formic acid, and 1.5 mL of 30 $H_2O_2$ was stirred at 70° for 40 min. The yellow-colored reaction mixture was then cooled to room temperature, diluted with water, and neutralized to pH 7.00 with concentrated ammonium hydroxide. Extraction of the neutralized solution with 3×100 ml portions of chloroform, drying the extracts (sodium sulfate), and concentration of the extracts afforded a yellowish-brown crude solid. Chromatography on silica gel employing 80:20 chloroform/hexane as the eluant afforded a white colored solid: 550 mg (69%) yield. An analytical sample was prepared by crystallization from diethyl ether/hexane: mp 118°-120° C.; TLC (chloroform), $R_f$=0.66, IR(KBr pellet), 2980, 1524, 1486, 1463, 1452, 1418, 1293, 1281, 1218, 803 cm$^{-1}$. $^1$H NMR (dimethyl sulfoxide-d$_6$)δ7.36 ABX, J$_{ortho}$=8.2 Hz, J$_{meta}$=0 Hz, $_{para}$=0 Hz, C(5) and C(6) aromatic protons respectively); 7.20 (1 H, s, C(8) proton), 4.04 (2 H, t, J~7 Hz, C(1) methylene), 2.90 (2 H, t, J~7.00 Hz, C(3) methylene), 2.61 (2 H, quintet, J 7 Hz, C(2) methylene), 2.40 (3 H, s, 7-methyl); mass spectrum (EI mode) m/z 172 (P+). Anal. Calcd for $C_{11}H_{12}N_2$: C, 72.91; H, 6.62: N, 15.45. Found: C, 73.31; H, 6.50; N, 15.34.

6-Bromo-7-methyl-2,3-dihydro-1H-pyrrolo[1,2-a]benzimidazole (12). To a solution of 1 g (5.81 mmol) of 11 in 30 mL of glacial acetic acid, heated at 100° C. was added 300 l of bromine in 3 mL glacial acetic acid. After the addition, the reaction mixture was heated at 100°-110° C. for 4 hours. The cooled reaction mixture was diluted with 100 mL of water and neutralized with aqueous sodium bicarbonate. The product crystallized from solution as a light yellow solid. Yield upon drying the collected solid was 1.37 g (88%). Recrystallization from chloroform/hexane afforded analytically pure 12: mp 167°-170° C.; TLC (chloroform/methanol, [90:10]), $R_f$=0.56, IR(KBr pellet), 2949, 2929, 1581, 1521, 1482, 1461, 1448, 1418, 1291, 872 cm$^{-1}$; $^1$H NMR (dimethyl sulfoxide-d$_6$) δ7.7, and 7.43 (2H, 2×s, aromatic protons), 4.04 (2H, t, J~7 Hz), C(1) methylene), 2.91(2H, t, J~7 Hz), C(3) methylene), 2.59 (2H, quintet, J~7 Hz, C(2) methylene), 2.39 (3H, s, 7-methyl); mass spectrum (EI mode) m/z 250 and 252 (P+, $^{79}$Br and P+, $^{81}$Br), 171(P+−Br). Anal. Calcd for $C_{11}H_{11}BrN_2$.0.25 $H_2O$: C, 51.47; H, 4.31; N, 10.91. Found: C, 51.56; H, 4.24; N, 10.78.

6-Bromo-7-methyl-5-nitro-2,3-dihydro-1H-pyrrolo[,1,2-a]benzimidazole (13). A solution of 245 mg (0.97 mmol) of 12 in a 5 mL mixture of fuming nitric acid and concentrated sulfuric acid (4:1) was stirred in an ice bath for 10 min.. The completed reaction was poured over cracked ice and the pH of resulting solution adjusted to 6.5 with aqueous sodium bicarbonate. Extraction of this solution with 3×50 mL portions of chloroform, drying the extracts (sodium sulfate), and then concentration afforded a yellow solid, 165 mg (57%). Recrystallization from chloroform/hexane afforded analytically pure material: mp 201°-203° C.; TLC (chloroform/methanol, [95:5]) $R_f$=0.61; IR(KBr pellet) 1537, 1517, 1449, 1413, 1383, 1374, 1342, 1297, 884, 860 cm$^{-1}$; $^1$H NMR (dimethyl sulfoxide-d$_6$) δ7.77 (1H, s, aromatic proton), 4.15 (2H, t, J~Hz, C(1) methylene), 2.99 (2H, t, J~7 Hz, C(3) methylene), 2.67 (2H, quintet, J~7 Hz, C(2) methylene); 2.52 (3H, s, 7-methyl); mass spectrum (EI mode) m/z 295 and 297 (P+, $^{79}$Br and $^{81}$Br), 249 and 251 (P+−NO$_2$). Anal. Calcd for $C_{11}H_{10}BrN_3O_2$: C, 44.60; H, 3.40; N, 14.18. Found: C, 44.83; H, 3.31; N, 14.07.

5-Amino-7-methyl-2,3-dihydro-1H pyrrolo[1,2-a]benzimidazole (14). A suspension of 550 mg (1.85 mmol) of 13 in 100 mL of methanol containing 90 mg of 5% palladium on carbon was shaken under 50 psi $H_2$ for 8 hours. The reaction mixture was filtered through Celite and the filter cake washed with methanol. Acidification of filterate with few drops of 1N HCl and evaporation in vacuo afforded the dihydrochloride salt of 14. Recrystallization was carried out from ethyl acetate/methanol: 350 mg (72%) yield; dec pt 320° C.; TLC (chloroform/methanol, [90:10]), $R_f$=0.39; IR(KBr pellet), 3369, 3316, 3206, 2918, 2886, 2871, 1652, 1569, 1495, 1386 cm$^{-1}$; $^1$H NMR (dimethyl sulfoxide-d$_6$) δ6.74 and 6.54 (2H, 2×s, C(6) and C(8) aromatic protons), 4.25 (2H, t, J~7 Hz, C(1) methylene), 3.30 (2H, t, J~7 Hz, C(3) methylene), 2.74 (2H, quintet, J~7 Hz, C(2) methylene), 2.33 (3H, H, s, 7-methyl); mass spectrum (EI mode) m/z 187 (P+ for 14). Anal. Calcd for $C_{11}H_{13}N_2$.2HCl.0.25 $H_2O$: C, 49.91; H, 5.71; N, 15.87. Found: C, 50.21; H, 5.29; N, 15.82.

7-Methyl-2,3-dihydro-1H-pyrrolo[1,2-a]benzimidazole-5,8-dione (15). To a suspension of 218 mg (0.83 mmol) of 15 in 10 mL of water, containing 200 mg of monobasic potassium phosphate, was added a solution of 1.34 g of Fremy's salt in 50 mL of water containing 500 mg of monobasic potassium phosphate. The reaction mixture was stirred at room temperature for 2 hours and extracted with 3×50 mL portions of chloroform. The dried extracts (sodium sulfate) were concentrated and then chromatographed over silica gel, employing chloroform as the eluant, to afford yellow-colored 14, 105 mg (61%) yield. Recrystallization from chloroform/hexane afforded analytically pure 15: mp 162°-164° C.; TLC (methanol chloroform[10:90]), $R_f$=0.62; IR(KBr pellet) 1675, 1659, 1647, 1515, 1154 cm$^{-1}$; $^1$H NMR (dimethyl sulfoxide-d$_6$) δ6.54 (1H, quartet, J=1.6 Hz, C(6) proton coupled to 7-methyl), 4.16 (2H, t, J~7 Hz, C(1) methylene), 2.86 (2H, t, J~7 Hz, C(3) methylene), 2.62 (2H, quintet, J~7 Hz, C(2) methylene), 2.00 (3H, d, J=1.6 Hz, 7-methyl coupled to C(6) proton); mass spectrum (EI mode) m/z 202 (P+), 174 (P+−CO). Anal. Calcd for $C_{11}H_{10}N_2O_2$: C, 65.33; H, 4.98; N, 13.85. Found: C, 65.15; H, 4.70; N, 13.61.

6-(N-Aziridinyl)-7-methyl-2,3-dihydro- 1H-pyrrolo 1,2-a]benzimidazole-5,8-dione (16). To a solution of 35 mg (0.17 mmol) of 15 in 4 mL of dry methanol, chilled at 0° C., was added 0.5 mL of ethyleneimine. The reaction was stirred at 0° for 30 min and then at room temperature for 1 hour. The solvent was removed in vacuo and the red residue flash chromatographed on silica gel using chloroform as the eluant. The purified product was recrystallized from chloroform/hexane: 20.5 mg (48%) yield; mp 192°-194° C. dec.; TLC (acetone), $R_f$=0.73; IR(KBr pellet) 1674, 1632, 1575, 1518, 1377, 1338, 1315, 1137, 988 cm$^{-1}$; $^1$H NMR (CDCl$_3$) δ4.17 (2H, t, J~7 Hz, C(1) methylene) 2.89 (2H, t, J~7 Hz, C(3) methylene), 2.65 (2H, quintet, J~7 Hz, C(2) methylene); 2.31 (4H, s, aziridine protons), 2.02 (3H, s, 7-methyl); mass spectrum (EI mode) m/z 243 (P+), 228 (P+−methyl). Anal. Calcd for $C_{13}H_{13}N_3O_2$: C, 64 18; H, 5.34; N, 17.27. Found: C, 64.02; H, 5.21; N, 16.76.

2,4-Dinitro-5-N-pyrrolidinotoluene (17). A mixture of 5-bromo-2,4-dinitrotoluene (2.61 g, 10 mmol) and pyrrolidine (2.49 g, 35 mmol) was heated at 90°-100° C. for 2 hours. The resulting dark brown oil was combined with cracked ice and the precipitated solids filtered off, washed with water, and vacuum dried. Purification was carried out by flash chromatography of the solids on a silica gel column using chloroform/hexane (50:50) as eluant. Evaporation of the eluants afforded 17 as orange needles: 2.0 g (82%) yield; mp 142° C.; TLC (chloroform), $R_f=0.82$; IR (KBr pellet) 1606, 1566, 1510, 1369, 1350, 1334, 1301, 1276, 1130, 833 cm$^{-1}$; $^1$H NMR (dimethyl sulfoxide-d$_6$) $\delta$8.83 and 8 53 (2H, 2×s, aromatic protons), 3.27 (4H, m, methylenes adjacent to pyrrolidine N), 2.61 (3H, s, methyl), 1.99 (4H, m, other pyrrolidine methylenes); mass spectrum (EI mode) m/z 251 (P+), 234 (P+ −OH). Anal. Calcd for $C_{11}H_{13}N_3O_4$: C, 52.58; H, 5.21; N, 16.72. Found: C, 52.51; H, 5 27; N, 16.64.

2,4-Diacetamido-5-N-pyrrolidinotoluene (18). A suspension of 1.2 g (4.78 mmol) of 17 and 120 mg of 5% Pd on charcoal in 20 mL of methanol was shaken under 50 psi H$_2$ for 4 hours. The mixture was then filtered through Celite and the filtrate combined with 10 mL of acetic anhydride. After stirring this solution for 1 hour, the solvent was removed in vacuo and ether added to crystallize the residue. Yield of crude product, suitable for the next step, was 1.05 g (81%). An analytical sample was prepared by recrystallization from chloroform/hexane: dec pt 234° C.; TLC (chloroform/methanol [80:20]), $R_f$ 0 61; IR (KBr pellet) 3261, 1651, 1616, 1526, 1491, 1464, 1454, 1416, 1368, 1280 cm$^{-1}$; $^1$H NMR (dimethyl sulfoxide-d$_6$) $\delta$9.11 and 9.02 (2H, 2×s, amide protons), 7.21 and 6.65 (2H, 2×s, aromatic protons), 3.11 (4H, m, methylenes adjacent to pyrrolidine nitrogen), 2.09, 1.99, and 1.98 (9H, 3×s, methyls), 1.84 (4H, m, other pyrrolidine methylenes); mass spectrum (EI mode) m/z 275 (P+), 232 (P+ −acetyl), 217 (P+ −acetamido). Anal. Calcd for $C_{15}H_{21}N_3O_2$: C, 65.42; H, 7.68; N, 5.26. Found: C, 65.00; H, 7.68; N, 15.00.

7-Methyl-6-nitro-2,3-dihydro-1H-pyrrolo[1,2-a]benzimidazole 3-Acetate (19). A mixture consisting of 2.5 g (10 mmol) of 17, 2.72 g (20 mmol) of ZnCl$_2$, and 10 mL of acetic anhydride was refluxed (90°-100° C.) for 4 hours. The reaction mixture was then cooled and combined with 100 mL of water. Extraction of the diluted reaction mixture with 3×50 mL portions of chloroform and concentration of the dried (sodium sulfate) extracts afforded crude product. Purification by silica gel chromatography, using ethyl acetate/methanol 95:5) as eluant, afforded pure 19 as a light yellow powder: 1.4 g (53%) yield; mp 172° C. dec; TLC (chloroform/methanol [90:10]) Rf=0.51; IR (KBr pellet) 1738, 1527, 1373, 1344, 1318, 1297, 1261, 1248, 1078, 1034 cm$^{-1}$; $^1$H NMR (dimethyl sulfoxide-d$_6$) $\delta$8.48 (1H, s, C(5) aromatic), 7.27 (1H, s, C(8) aromatic), 6.20 (1H, dd, J=7.6 Hz, J=3.8 Hz, C(3) proton), 4.31 and 4.17 (2H, 2 m, C(1) diastereomeric methylene), 3.24 and 2.72 (2H, 2 m, C(2) diastereomeric methylene), 2.72 (3H, s, 7-methyl), 2 15 (3H, s, acetate methyl); mass spectrum (EI mode), m/z 275 (P+), 258 (P+ −OH), 232 (P+ −acetyl). Anal. Calcd for $C_{13}H_{13}N_3O_4$: C, 56.67; H, 4.72; N, 5.27. Found: C, 56.61 H, 4.72; N, 14.97.

6-Acetamido-7-methyl-2,3-dihydro-1H-pyrrolo[1,2-a]benzimidazole 20). A mixture of 1 g (3.63 mmol) of 18, 6 mL of 96% formic acid, and 3 mL of 30% hydrogen peroxide was stirred at 70° C. for 30 min. The reaction mixture color changed from blue to red-brown, and finally to yellow upon completion. The reaction mixture was then diluted with water and neutralized to pH 7.00 with concentrated ammonium hydroxide. Extraction of the neutralized solution with 2×50 mL portions of chloroform, drying the extracts (sodium sulfate), and concentration afforded crude 20 as a yellow solid. Recrystallization was carried out from chloroform/hexane: 676 mg (81%) yield; dec pt 200° C.; TLC (chloroform/methanol [90:10]), $R_f=0.42$; IR (KBr pellet) 3442, 3230, 1668, 1526, 1476, 1456, 1423, 1309, 1304, 1283 1; cm$^{-1}$H NMR (dimethyl sulfoxide-d$_6$) 9.23 (1H, s, amide proton), 7.45 and 7.23 (2H, 2×s, aromatic protons), 4.04 (2H, t, J~7 Hz, C(1) methylene), 2.91 (2H, t, J~7 Hz, C(3) methylene), 2.61 (2H, quintet, J~7 Hz, C(2) methylene), 2.26 (3H, s, 7-methyl), 2.04 (3H, s, acetate methyl); mass spectrum (EI mode) m/z 229 (P+), 187 (P+ −ketene). Anal. Calcd for $C_{13}H_{15}N_3O.0.5H_2O$: C, 65.47; H, 6.76; N, 17.62. Found: C, 65.90; H, 6.59; N, 17.75.

6-Acetamido-7-methyl-2,3-dihydro-1H-pyrrolo [1,2-a]benzimidazole-3-Acetate (2). A solution of 1.1 g (3.99 mmol) of 19 in 200 mL of methanol was shaken under 50 psi H$_2$ in the presence of 200 mg of 5% Pd on carbon for 4 hours. The completed reaction was filtered through Celite into a flask containing 2 mL of acetic acid. The filtrate was then evaporated in vacuo to an acetic acid/amine mixture, to which was added 6 mL of acetic anhydride. This mixture was stirred for 30 min at room temperature, and then diluted with 200 mL of diethyl ether. Pure 21 crystallized from the ether solution after chilling for several hours: 809 mg (70%) yield. Recrystallization was carried out from a large volume of hot ethyl acetate: dec pt 232° C.; TLC (1-butanolacetic acid-water [5:2:3]), $R_f=0.4$; IR (KBr pellet) 3260, 1741, 1647, 1537, 1368, 1233, 1145, 1131 cm$^{-1}$; $^1$H NMR (dimethyl sulfoxide-d$_6$) 9.28 (1H, s, amide proton), 7.57 and 7.37 (2H, 2×s, aromatic protons), 6.10 (1H, dd, J=7.6 Hz, J=3.2 Hz, C(3) proton), 4.22 and 4.12 (2H, 2×m, C(1) diastereomeric methylene), 3.11 and 2.55 (2H, 2×m, C(2) diastereomeric methylene), 2.29 (3H, s, 7-methyl), 2.07 and 2.05 (6H, 2×s, acetate and acetamido methyls).

6-Acetamido-7-methyl-5-nitro-2,3-dihydro-1H-pyrrolo[1,2-a]benzimidazole (22a). To a mixture of 5.4 mL of fuming nitric acid and 0.6 mL of concentrated sulfuric acid, chilled at 0° C., was added 600 mg (2.61 mmol) of 20. The reaction mixture was stirred at 0° C. for 5 min and then poured into a mixture of 20 g of cracked ice and 30 mL of chloroform. The mixture was neutralized with saturated aqueous sodium bicarbonate and vigorously stirred to extract the product into the chloroform layer. The chloroform layer was removed and the aqueous layer extracted with 3×30 mL portions of chloroform. Drying the combined chloroform extracts (sodium sulfate) and concentration afforded 22a as a yellow solid. Recrystallization was carried out from chloroform/hexane: 500 mg (69%) yield; m.p. 198° C.; TLC (chloroform/methanol [85:15]), $R_f=0.44$; IR (KBr pellet) 1689, 1525, 1517, 1492, 1459, 1421, 1369, 358, 1263, 1249 cm$^{-1}$; $^1$H NMR (CDCl$_3$) $\delta$7.89 (1H, s, amide proton), 7.38 (1H, s, C(8) proton), 4.14 (2H, t, J=7.4 HZ, C(1) methylene), 3.14 (2H, t, J=7.4 Hz, C(3) methylene), 2.78 (2H, quintet, J=7.4 Hz, C(2) methylene), 2.41 (3H, s, 7-methyl), 2.21 (3H, s, acetamido methyl); mass spectrum (EI mode) m/z 274 (P+), 256 (P+ −H$_2$O), 232 (P+ −ketene), 228 (P+ −NO$_2$). Anal. Calcd for $C_{13}H_{14}N_4O_3.1.5 H_2O$: C, 51.84; H, 4.68; N, 18.59. Found: C, 51.64; H, 4.68; N, 18.52.

6 Acetamido-7-methyl-5-nitro-2,3-dihydro-1H-pyrrolo[2-a]benzimidazole-3-Acetate (22b). To a mixture of 2 mL of fuming nitric acid and 0.8 mL of concentrated sulfuric acid, chilled in a dry-ice acetone bath, was added 400 mg (1.39 mmol) of 21 portionwise over a two min period. The reaction mixture was removed from the ice bath and stirred for 15 min while coming to room temperature and then poured into a mixture of 50 g ice and 50 mL of chloroform. Saturated sodium bicarbonate was added to the above mixture with vigorous stirring until the pH was neutral. The chloroform layer was separated and the aqueous layer extracted 2× with 50 mL portions of chloroform. Drying the combined extracts (sodium sulfate), concentration to a residue, and trituration with ethyl acetate afforded crystalline 22b: 310 mg (67%) yield. Recrystallization was carried out from chloroform/hexane: mp 204° C.; TLC (chloroform/methanol [9;1]), $R_f=0.24$; IR (KBr pellet) 1750, 1681, 1528, 1370, 1360, 1270, 1083 cm$^{-1}$; $^1$H NMR (CDCl$_3$) $\delta$7.89 (1H, s, amide proton), 7.47 (1H, s, C(8) proton), 6.17 (1H, dd, J=7.5 Hz, J=3.5 Hz, C(3) proton), 4.2 (2 H, m, C(1) diastereomeric methylene), 3.17 and 2.72 (2H, 2×m, C(2) diastereomeric methylene), 2.43 (3H, s, 7-methyl) 2.22 and 2.13 (6H, 2×s, acetate and acetamido protons); mass spectrum (EI mode) m/z 332 (P+), 314 (P+−H$_2$O), 286 (P+−NO$_2$). Anal. Calcd for C$_{15}$H$_{16}$N$_4$O$_5$.0.25 H$_2$O: C, 53.49; H, 4.93; N, 16.62. Found: C, 53.78; H, 4.62; N, 16.42.

7-Acetamido-5-amino-7-methyl-2,3-dihydro-1H-pyrrolo[1,2-a]benzimidazole (23a) and the 3-Acetate Derivative (23b). A solution of 1.2 mmol of 22a or 22b in 60 mL of methanol was shaken under 50 psi H$_2$ in the presence of 40 mg of 5% Pd on carbon for 2.5 hours. The catalyst was removed by filtration through Celite and the filtrate concentrated to a yellow oil. Dissolution of the oil in 15 mL of chloroform, addition of hexane until the solution became cloudy, and then chilling afforded the amine as a white crystalline solid.

Reduction of 22a afforded 23b in 74% yield: dec pt 235° C.; TLC (chloroform/methanol [8:2]), $R_f=0.58$; IR (KBr pellet) 3362, 3216, 3209, 1669, 1634, 1552, 1533, 1305, 1297, 1277 cm$^{-1}$; $^1$H NMR (dimethyl sulfoxide-d$_6$) 9.10 (1H, s, amide proton), 6.76 (1H, s, C(8) proton), 4.23 (2H, t, J=7.2 Hz, C(1) methylene), 3.28 (2H, t, J=7.6 Hz, C(3) methylene), 2.74 (2H, quintet, J∼7.4 Hz, C(2) methylene), 2.18 (2H, s, 7-methyl), 2.03 (3H, s, acetate methyl); mass spectrum (EI mode) m/z 244 (P+), 229 (P+-methyl), 201 (P+-acetyl). Anal. Calcd for C$_{13}$H$_{16}$N$_4$O0.6 H$_2$O: C, 61.21; H, 679; N 6.79; N, 21.95. Found: 61.13; H, 6.13; N, 21.49.

Reduction of 22b afforded 23b in 77% yield: dec pt. 211° C.; TLC (chloroform/methanol [80:20]), $R_f=0.48$; IR (KBr pellet) 3440, 3399, 1738, 1663, 1620, 1491, 1235 cm$^{-1}$; $^1$H NMR (dimethyl sulfoxide-d$_6$) $\delta$8.89 (1H, s, amide proton), 6.64 (1H, s, C(8) proton), 6.08 (1H, dd, J=7.5 Hz, J=3 Hz, C(3) proton), 4.96 (2H, br s, amine protons), 4.14 and 4.05 (2H, 2×m, C(1) diastomeric methylene), 2.16 (3H, s, 7-methyl), 2.06 and 2.04 (6H, 2×s, acetate and acetamido methyls); mass spectrum (EI mode) m/z 302 (P+). Anal. Calcd for C$_{15}$H$_{18}$N$_4$O$_3$.0.5 H$_2$O: C, 58.30; H, 6.15; N, 17.98. Found: C, 58.61; H, 5.78; N, 17.76.

6-Acetamido-7-methyl-2,3-dihydro-1H-pyrrolo [1,2-a]benzimidazole-5,8-dione (1a) and the 3-Acetate Derivative (1b). To a suspension of 23a or 23b (0.7 mmol) in 10· mL of water, containing 200 mg of potassium phosphate monobasic, was added a solution of 1 g of Fremy's salt in 30 mL of water containing 500 mg of potassium phosphate monobasic. The mixture was stirred at room temperature for 2.5 hours and then extracted 3×with 100 mL portions of chloroform. dried extracts (sodium sulfate) were concentrated to a yellow solid, which was recrystallized from chloroform/hexane.

Oxidation of 23a afforded 1a in 71% yield: dec pt 194° C.; TLC (acetone), $R_f=0.41$; IR (KBr pellet) 2860, 1651, 1539, 1518, 1485, 1466, 1310, 1279, 1245, 1099 cm$^{-1}$; $^1$H NMR (CDCl$_3$) $\delta$7.70 (1H br s, amide proton), 4.24 (2H, t, J=7.0 Hz, C(1) methylene), 2.84 (4H, m, C(2) and C(3) methylenes), 2.24 (3H, s, 7-methyl), 1.96 (3H, s, acetamido methyl); $^{13}$C NMR (CDCl$_3$) 178.0, 177.7, 167.6, 160.9, 143.9, 135.9, 131.1, 130.6, 45.2, 26.5, 24.2, 22.8, 13.5 cps; mass spectrum (EI mode) m/z 259 (P+), 244 (P+-methyl), 217 (P+-ketene). Anal. Calcd for C$_{13}$H$_{13}$N$_3$O$_3$: C, 60.22; H, 5.05; N, 16.20. Found: C, 60.04; H, 4 98; N, 15.93.

Oxidation of 23b afforded 1b in 27% yield: dec pt 221° C.; TLC (acetone), $R_f=0.56$; IR (KBr pellet) 1730, 1695, 1659, 1610, 1520, 1371, 1314, 1284, 1244, 1083; $^1$H NMR (CDCl$_3$) $\delta$7.69 (1H, br s, amide proton), 6.09 (1H, dd, J=7.7 Hz, J=3.3 Hz, C(3)-proton), 4.37 (2H, m, C(1) diastereomeric methylene), 3.18 and 2.72 (2H, 2×m, C(2) diastereomeric methylene), 2.25 (3H, s, 7-methyl), 2.10 and 1.98 (6H, 2×s, acetate and acetamido methyls); $^{13}$C NMR (dimethyl sulfoxide-d$_6$) $\delta$177.3, 176.6, 169 5, 167.9, 156.8, 43.9, 138, 133.5, 129.9, 66.3, 43.5, 34.0, 22.9, 20.5, 12.2 cps; mass spectrum (EI mode) m/z 317 (p+), 300 (P+−OH), 275 (P+-ketene). Anal. Calcd for C$_{15}$N$_{15}$N$_3$O$_5$: C, 56.78; H 4.76; N, 13.27. Found: C, 56.59; H, 4.67; N, 12.87.

syn/anti 6 Acetamido-5-imino-7-methyl-2,3-dihydro 1H-pyrrolo[2-a]benzimidazol-8-one (2a). To a suspension of 100 mg (0.4 mmol) of 23a in 10 mL of 0.2M pH 7.0 phosphate buffer ($\mu$=1.0, KCl) was added a suspension of 500 mg of Fremy's salt in 20 mL of the same buffer. To assist in dissolution of the Fremy's salt, 20 mL of water was then added to the above mixture. While stirring the mixture at room temperature, purple syn 2a crystallized from solution. After 30 min, the syn 2a was filtered off and dried: 69 mg (65%) yield. The filtrate was extracted with 2×50 mL of chloroform to remove the anti isomer. Drying the extracts (sodium sulfate), evaporation to a solid residue, and finally recrystallization from chloroform/hexane afforded 10 mg (9.5%) of yellow anti 2a. Extensive purification of either isomer was not possible due to syn/anti introconversion in many solvents.

Physical properties of syn 2a: dec pt 260° C.; TLC (chloroform/methanol [90:10]), $R_f=0.44$; IR (KBr) 3250, 1652, 1625, 1608, 1422, 1393 cm$^{-1}$; $^1$H NMR dimethyl sulfoxide-d$_6$) $\delta$9.19 and 6.62 (2H, 2×br s, imine protons, see Scheme 3), 4.12 (2H, m, C(1) methylene), 2.8and 2.58 (4H, 2×m, C(2) and C(3) methylenes), 1.72 and 1.58 (6H, 2×s, 7-methyl and acetamido methyls); $^{13}$C NMR (dimethyl sulfoxide-d$_6$) $\delta$176.5, 158.6, 154.3, 149.5, 138.8, 129.8, 110.4, 96.2, 44.5, 26.1, 25.7, 22.2, 8.7 cps; mass Spectrum (EI mode) m/z 258 (P+), 243 (P+−methyl), 229 (P+−C=NH), 215 (P+−acetyl). Anal. Calcd for C$_{13}$H$_{14}$N$_4$O$_2$.1.25 H$_2$O: C, 55.60; H, 5.69; N, 19.95. Found: C, 55.35; H, 5.12; N, 19.07.

Physical properties of anti 2a: dec pt 245° C.; TLC, same as syn 2a; IR (KBr pellet) 3260, 3200, 1683, 1644, 1625, 1504, 1484, 1465, 1422, 1341, 1314, 1252 cm$^{-1}$; $^1$H NMR (dimethyl sulfoxide-d$_6$) $\delta$11.42 (1H, s, imine proton), 9.57 (1H, s, amide proton), 4.19 (2H, t, J=6.8 Hz, C(1) methylene), 2.73 (4H, m, C(2) and C(3) methylenes), 2.07 and 1.81 (6H, 2×s, 7-methyl and acetamido methyl); mass spectrum (same as syn 2a).

syn/anti 6-Acetamido-5-imino-7-methyl-2,3-dihydro-1H-pyrrolo[1,2-a]benzimidazol-8-one-3-Acetate (2b). To a solution of 23b, 150 mg (0.49 mmol), in 25 mL of 0.2M pH 7.0 phosphate buffer ($\mu=1.0$, KCl) was added 708 mg of Fremy's salt. The mixture was stirred at room temperature for 1 hour, during which time red syn 2b crystallized from solution. Filtration, washing the solids with a small volume of water, and then drying afforded syn 2b as a fiberous red solid: 61 mg (36%) yield. The filtrate was extracted with 2×50 mL of chloroform. Evaporation of the dried extracts (MgSO$_4$) to a residue and then trituration with acetone afforded yellow anti 2b (21 mg (12%) yield).

Physical properties of syn 2b: dec pt 312° C.; TLC (acetone), R$_f$0.57; IR (KBr pellet) 3340, 1745, 1625, 1601, 1380, 1238 cm$^{-1}$; $^1$H NMR (dimethyl sulfoxide-d$_6$) $\delta$9.34 and 6.68 (2H, 2×br s, imine protons), 5.99 (1H, m, C(3) proton), 4.24 (2H, m, C(1) diastereomeric methylene), 3.04 and ~2.5 (2H, 2 x m, C(2) diastereomeric methylene), 2.07 (3H, s, 7-methyl), 1.74 and 1.54 (6H, 2×s, acetate and acetamido methyls); $^{13}$C NMR (dimethyl sulfoxide-d$_6$) $\delta$176.2, 169.6, 154.7, 154.1, 149.8, 138.7, 130, 110.6, 96.8, 65.5, 43.3, 34.1, 25.5, 20.6, 8.7 cps; mass spectrum (EI mode) m/z 316 (P+). Anal. Calcd for C$_{15}$N$_{16}$N$_4$O$_4$0.25 H$_2$O: C, 56.15; H, 5.18; N, 17.45. Found: C, 55.94; H, 5.19; N, 17.18.

Physical properties of anti 2b: dec pt 304° C.; TLC (same as syn 2b); IR KBr pellet) 3188, 1740, 1714, 1644, 1627, 1487, 1376, 1310, 1230 cm$^{-1}$; $^1$H NMR (dimethyl sulfoxide-d$_6$) $\delta$11.65 (1H, s, amide proton), 9.64 (1H, s, imine proton), 6.06 (1H, dd, J=8 Hz, J=3.8 Hz, C(3) proton), 4.29 (2H, m C(1) diastereomeric methylene), 2.08 (6H, 2×s) and 1.8 (3H, s), 7-methyl, acetamido and acetate methyls, no assignments made; mass spectrum (same as syn 2a).

The azamitosenes and iminoazamitosenes, as demonstrated, have a free hydroxyl group available at the three position for derivatization. Thus acyl derivatives of the azamitosenes and iminoazamitosenes can be used for the same biological purpose as the parent compounds.

Acids which can be used in the acylation of azamitosenes and iminoazamitosenes include:

(a) saturated or unsaturated, straight or branched chain aliphatic carboxylic acids, for example, acetic, propionic, butyric, isobutyric, tert-butyl-acetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropioplic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or loweralkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid; and chloropropionic acid; and bromobutyric acid; - and -iodovaleric acid; mevalonic acid; 2- and 4-chlorocyclohexanecarboxylic acid; shikimic acid; 2-nitro- 1-methylcyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2- methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid;5,6-dibromo-2-methyl-cyclohexanecarboxylic acid; 3-bromo-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcycohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4'-dichlorobenzilic acid; o-, m-, and p-nitrobenzoic acid; cyanocetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicyclic acid; mandelic acid, levulinic acid; pyruvic acid; glycine; alanine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; asparagine; and the like.

The administration of azamitosenes and iminoazamitosenes, and their pharmaceutically active, physiologically compatible derivatives is useful for treating animals or humans afflicted with a neoplastic disease, such as, for example, acute myelocytic leukemia, acute lymphocytic leukemia, malignant melanoma, adenocarcinoma of lung, neuroblastoma, small cell carcinoma of lung, breast carcinoma, colon carcinoma, gastric carcinoma, ovarian carcinoma, bladder carcinoma, hematologic malignancies and the like.

The fresh human tumor data hereinafter reported have been found to be predictors of clinical activity in humans. Testing a cancer retardation drug on an excised human tumor provides more accurate prediction of the efficacy of the drug in vivo than if the testing is done merely on human cell lines. As described in the literature cited, data show that the efficacy of the drug on excised human tumors is directly correlated to the efficacy of that drug when used in a human cancer patient. Therefore, the data hereinafter reported using fresh human tumors demonstrate that the present invention is effective for treating neoplastic disease in humans.

In vitro primary drug screening was carried out at the National Cancer Institute (NCI) employing microculture assays for cell growth/viability. The development of these assays has been described by Boyd, M. R.: Status of the NCI Preclinical Antitumor Drug Discovery Screen. *Principles & Practices of Oncology* 3.1, 1989.

The cell growth/viability was assessed with the dye sulforhydramine B (SRB) which is an indicator of cell number SRB is a bright pink anionic dye that, in dilute acetic acid, binds electrostatically to the basic amino acids of TCA-fixed cells. Details of the SRB assay procedure are provided elsewhere.

The modus operandi for the screening process is briefly described below:

In the routine Stage I screening, each agent is tested over a broad concentration range against every cell line in the current panel. All lines are inoculated onto a series of standard 96-well microtitre plates on day 0, in the majority of cases at 20,000 cells/well, then preincubated in absence of drug for 24 hours. Test drugs are then added in five tenfold dilutions starting from the highest soluble concentration, and incubated for a further 48 hours. Following this, the cells are fixed in situ, washed, and dried. SRB is added, followed by further washing and drying of the stained adherent cells mass. The bound stain is solubilized and measured spectrophotometrically on automatic plate readers interfaced with microcomputers, which in turn are interfaced to a mainframe computer.

Further details of this procedure are reported in the Monks, A. et al; Implementation of a pilot-scale, high-flux anticancer drug screen utilizing disease-oriented panels of human cell lines in culture. *Proc. Am. Associ. Cancer Res.* 30:607, 1989.

The graphical depiction of screening results shown in the following tabvles II-IX and correlated to EXAMPLES 13-16, inclusive, is explained below (See: NCI document entitled *Screening Data Report Components*).

Mean graphs facilitate visual scanning of data for potential patterns of selectivity for particular cell lines or for particular subpanels with respect to a selected response parameter. Differences in apparent selectivity patterns may occur for the same compound against the cell lines when different parameters are compared. The mean graphs page of the data package shows mean graphs at each of the principal response parameters: GI50, TGI, and LC50. Bars extending to the right represent sensitivity of the cell line to the test agent in excess of the average sensitivity of all tested cell lines. Since the bar scale is logarithmic, a bar 2 units to the right implies the compound achieved the response parameter (e.g., GI50) for the cell line at a concentration one-hundredth the mean concentration required over all cell lines, and thus the cell line is unusually sensitive to that compound. Bars extending to the left correspondingly imply sensitivity less than the mean. If, for a particular drug and cell line, it was not possible to determine the desired response parameter by interpolation, the bar length shown is either the highest concentration tested (and the listed $\log_{10}$ of the response parameter will be preceded by a ">") or the lowest concentration tested (and the listed $\log_{10}$ will be preceded by a "<").

The values at either limit (> or >) are also calculated in the mean used for the meangraph. Therefore, the mean used in the meangraph may not be the actual means of the GI50, for instance. For this reason, we shall refer to this value as the MG_MID (for meangraph midpoint)."

The Dose-Response Matrix

The dose-response matrix combines some qualities of the dose-response curve with some qualities of the mean graph. Selective effects at the cell line or subpanel levels are visualized as in the mean graph, however, different levels of effect are also depicted simultaneously, as in dose response curves. Each column of the matrix corresponds to the drug effect at one of the five concentration levels, and each row corresponds to the effect against each cell line. Thus, each block within a row depicts the effect of a given concentration against a given cell line. The shading given the block depends on the value of the PG (percent growth) for the given concentration against the given cell line in comparison with the corresponding values for the GI150, TGI, and LC50. If the PG $> +50$, the block is white. If the PG $< -50$, the block is black. Two intermediate shades of gray are used if $+50 > PG > 0$ or if $0 < PG < -50$. Blocks for missing values have a period (.) in the center.

It is known ot those skilled in the art of discovering and developing new anticancer drugs that the in vitro human tumor drug screening methodology described herein provides a strong indication of the extent of clinical activity to be obtained by a candidate drug. Thus:

The availability of a wide variety of human tumor cell lines representing many different forms of human cancer seemed to offer an attractive basis for development of a disease-oriented in vitro primary screen. Moreover, since many established human tumor cell lines could be propagated in vivo in athymic, nude mice, there appeared the basis for an ideal disease-specific Stage II preclinical screening strategy. Thus, the basic concept for the new experimental primary drug screen required an in vitro primary screen comprised of a diverse panel of human tumor cell lines arrayed in disease-specific subpanels. (see; Wunz, T. P. et al, *J. Natl Cancer Inst.* 1990,82, 110; Von Hoff, D. D., *J. Natl. Cancer Inst.*, 1990, 82, 96; Von Hoff, D. D. et al, *J. Natl. Cancer Inst.* 1990, 82, 110; Alberts, D. S. et al, *Lancet*, 980, 2, 340.) The protocol for utilizing fresh human tumor to obtain meaningful data for design of useful therapeutic agents is well known and need not be detailed here. (see: Salmon, S. E. et al, *Cancer Treat Rep.*, 1981, 65, 102; Salmon, S. E. et al, *N. Enol. J. Med.*, 1978, 298, 1231; and Albert, DS, *Cancer Chemother Pharmacol.* 1981, 6, 253). The protocol employed for MTT assays are reported. (see: Mossman T. J. *Immunol Methods.* 1983, 65, 55).

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous and intra-arterial 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/kg. As used herein, mg/kg means weight of active ingredient in milligrams divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures.

To further aid in the understanding of the present invention and not by way of limitation, the following examples are presented.

EXAMPLE I

Several dosage forms were prepared embodying the present invention. They are shown in the following examples in which the notation "active ingredien" signifies azamitosenes, the iminoazamitosenes, their synthetic counterparts and the non-toxic pharmaceutically active derivatives thereof.

COMPOSITION "A"

Hard-Gelatin Capsules

One thousand two-piece hard gelatin capsules for oral use, each capsule containing 20 mg of an active ingredient are prepared from the following types and amounts of ingredients:

| Active ingredient, micronized | 20 gm |
|---|---|
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 mg amounts by substituting 5 gm, 25 gm and 50 gm of an active ingredient for the 20 gm used above.

COMPOSITION "B"

Soft Gelatin Capsules

One-piece soft gelatin capsules for oral use, each containing 20 mg of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient are prepared from the following types and amounts of ingredients.

| Active ingredient micronized | 20 gm |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 gm and 10 gm of an active ingredient for the 20 gm used above.

COMPOSITION "D"

Oral Suspension

One thousand ml of an aqueous suspension for oral use, containing in each teaspoonful (5 ml) dose, 5 mg of an active ingredient, is prepared from the following types and amounts of ingredients:

| Active ingredient micronized | 1 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. | 1000 ml |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml, 30 mg of an active ingredient for treating a neoplastic disease, is prepared from the following types and amounts of ingredients:

| Active ingredient, micronized | 30 gm |
|---|---|
| Polysorbate 80 | 5 gm |
| Methylparaben | 2.5 gm |
| Propylparaben | 0.17 gm |
| Water for injection, q.s. | 1000 ml |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of milliliter (1 M) three times a day.

COMPOSITION "F"

Suppository, Rectal and Vaginal

One thousand suppositories, each weighing 2.5 gm and containing 20 mg of an active ingredient are prepared from the following types and amounts of ingredients:

| Active ingredient, micronized | 1.5 gm |
|---|---|
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation is prepared, containing 20 mg of an active ingredient per ml of suspension, from the following types and amounts of ingredients:

| Active ingredient, micronized | 1.5 gm |
|---|---|
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "J"

Insufflation

Ten grams of an active ingredient in bulk form is finely divided by means of an air micronizer.

The foregoing composition is useful for treating a neoplastic disease, by the inhalation of 30 mg one to four times per day.

COMPOSITION "K"

Hard Gelatin Capsules

One hundred two-piece hard gelatin capsules for oral use, each capsule containing 20 mg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25 and 50 mg amounts by substituting 5 gm, 25 gm and 50 gm of the active ingredient for the 20 gm used above.

EXAMPLE 2

6-(N-Aziridinyl)-7-methyl-2, 3-dihydro -1H-pyrrolo [1, 2-a] benzimidazole-5, 8-dione-3-acetate (1c) was screened for in vitro activity against doxorubicin-sensitive ovarian cancer (2780/S) and 110-fold doxorubicin-resistant ovarian cancer (2780/DOX). The results of these assays indicate the said compound possesses cross sensitivity with doxorubicin and antitumor activity much greater than mitomycin C (MMC): $IC_{50}$ values of 16nM against 2780/DOX and 0.6nM against 2780/S, for 1c, and IC50 values of 200 nM against 2780/DOX and 100 nM against 2780/S for MMC.

EXAMPLE 3

6-(N-Aziridinyl)-7-methyl-2, 3-dihydro - 1H-pyrrolo [1, 2-a] benzimidazole-5, 8-dione-3-carbamate (1d) was screened for in vitro activity against doxorubicin-sensitive (2780/S) and doxorubicin-resistant (2780/DOX) ovarian cancer. The results of these assays indicate that the change from acetate 1c to carbamate 1d results in a substantial loss of cross sensitivity with doxorubicin and a decrease in potency to a level comparable with that of mitomycin C: $IC_{50}$ values of 200nM against 2780/DOX and 100 nM against 2780/S.

EXAMPLE 4

6-(N-Aziridinyl)-7-methyl-2, 3-dihydro -1H-pyrrolo [1, 2-a] benzimidazole-5, 8-dione-3-acetate (1c) was screened for in vitro activities against cisplatin-sensitive (2008/S) and cisplatin-resistant (2008/R) ovarian cancers. The results of these assays indicate that 1c is equally active against the sensitive and resistant strains of this cancer ($IC_{50}=7nM$) and possesses activity far greater than mitomycin C ($IC_{50}$ value not attainable).

EXAMPLE 5

6-(N-Aziridinyl)-7-methyl-2, 3-dihydro -1H-pyrrolo [1, 2-a] benzimidazole-5, 8-dione-3-carbamate (1d) was screened for in vitro activity against cisplatin-sensitive (2008/S) and cisplatin-resistant (2008/R) ovarian cancers. The results of these assays indicate that the change from acetate 1c to carbamate (1d) results in a complete loss of activity ($IC_{50}$ value for (1d) was not attainable).

EXAMPLE 6

6-(N-Aziridinyl)-7-methyl-2, 3-dihydro - 1H-pyrrolo [1, 2-a] benzimidazole-5, 8-dione-3-acetate (1c) was screened for in vitro activity against WiDr human colon cancer. The result of this assay indicates that 1c possesses greater antitumor activity against this cancer than mitomycin C (MMC): $IC_{50}$ values of 6nM and 20nM for (1c) and MMC respectively.

EXAMPLE 7

6-(N-Aziridinyl)-7-methyl-2, 3-dihydro - 1H-pyrrolo [1, 2-a] benzimidazole-5, 8-dione-3-acetate (1c) was screened for in vitro activity against SW480 human colon cancer. The results of this assay indicate that 1c possesses activity against this cancer comparable to mitomycin C (MMC): IC$_{50}$ values of 9nM and 7nM for (1c) and MMC respectively.

EXAMPLE 8

6-(N-Aziridinyl)-7-methyl-2, 3-dihydro - 1H-pyrrolo [1, 2-a] benzimidazole-5, 8-dione-3-carbamate (1d) was screened for in vitro activity against WiDr/S human colon cancer. The result of this assay indicates that 1d possesses less antitumor activity against this cancer than mitomycin C (MMC): IC$_{50}$ values of 100 nM and 20 nM for 1d and MMC respectively.

EXAMPLE 9

6-(N-Aziridinyl)-7-methyl-2, 3-dihydro - 1H-pyrrolo [1, 2-a] benzimidazole-5, 8-dione-3-carbamate (1d) was screened for in vitro activity against SW480 human colon cancer. The result of this assay indicates that 1d is somewhat less potent than mitomycin C(MCC): IC$_{50}$ values of 19nM and 7nM for 1d and MMC respectively.

EXAMPLE 10

6-(N-Aziridinyl)-7-methyl-2, 3-dihydro - 1H-pyrrolo [1, 2-a] benzimidazole-5, 8-dione-3-acetate (1c) was screened for in vitro activity against 8226/S human myeloma. The result of this assay indicates that 1c is somewhat more potent than mitomycin C (MCC): IC$_{50}$ valves of 100 nM and 200 nM for 1c and MMC respectively.

EXAMPLE 11

6-(N-Aziridinyl)-7-methyl-2, 3-dihydro - 1H-pyrrolo [1, 2-a] benzimidazole-5, 8-dione-3-carbamate (1d) was screened for in vitro activity against 8226/S myeloma. The results of this assay indicate that 1d is somewhat more potent than mitomycin C (MMC): IC$_{50}$ valves of 140nM and 200nM for 1d and MMC respectively.

EXAMPLE 12

Fresh ovarian tumors were collected from twelve (12) confirmed ovarian cancer patients. Azimitosene 1c was tested in vitro using the clonogenic assay described by Salmon et al, Salmon et al, and Albert et al (op cit). The IC$_{50}$ data (the drug concentration required to obtain 50% inhibition of tumor colony formation after 1 hour exposure to test compound) obtained from these assays are shown in Table 1.

TABLE I

| Patient No. | IC$_{50}$ (µg/mL) | Patient No. | IC$_{50}$ (µg/mL) |
|---|---|---|---|
| 1 | 0.085 | 7 | unachievable |
| 2 | 1.53 | 8 | 0.0074 |
| 3 | 0.0044 | 9 | 0.00437 |
| 4 | 0.0985 | 10 | 0.821 |
| 5 | 0.0165 | 11 | 0.0856 |
| 6 | 0.004 | 12 | 1.53 |

From this data it is apparent that 91% of ovarian cancers respond to 1c at a median IC$_{50}$ value of 0.05 ug/mL.

EXAMPLE 13

6-Acetamido-7-methyl-2,3-dihydro-1H-pyrrolo [1,2-a]benzimidazole-5,8-dione [Compound 1a] possesses a midrange GI50 of $10^{-5.84}$ M in 59 cell lines, exhibiting activity against leukemia, non-small cell lung cancer, small cell lung cancer, colon cancer, CNS cancer, melanoma, ovarian cancer, and renal cancer [See Tables II and III).

EXAMPLE 14

6-(N-aziridinyl)-7-methyl-2,3-dihydro-1H-pyrrolo [1,2-a]benzimidazole-5,8-dione-3-Acetate (Compound 1c) possesses a midrange GI50 of $10^{-7.94}$M in 59 cell lines, exhibiting activity against non-small cell lung, small cell lung cancer, colon cancer, CNS cancer, melanoma, ovarian cancer, and renal cancer. Only modest activity was observed in the leukemia panel (See Tables IV and V).

EXAMPLE 15

6-N-Aziridinyl-7-methyl-2,3-dihydro-1H-pyrrolo [1,2-a]benzimidazole-5,8-dione-3-Carbamate (Compound 1d) possesses a midrange GI of $10^{-5.78}$M in 59 cell lines exhibiting modest activity against non-small cell lung cancer, small cell lung cancer, colon cancer, CNS cancer, melanoma, ovarian cancer, and renal cancer. This compound had poor activity in the leukemia panel (See Tables VI and VII).

EXAMPLE 16

6-(N-Aziridinyl)-7-methyl-2,3-dihydro-1H-pyrrolo [1,2-a]benzimidazole-5,8-dione [Compound 16] possesses a midrange GI50 of $10^{-7.54}$M in 59 cell lines exhibiting activity against leukemia, non-small cell lung cancer, small cell lung cancer, colon cancer, CNS cancer, melanoma, ovarian cancer, renal cancer (See tables VIV and IX).

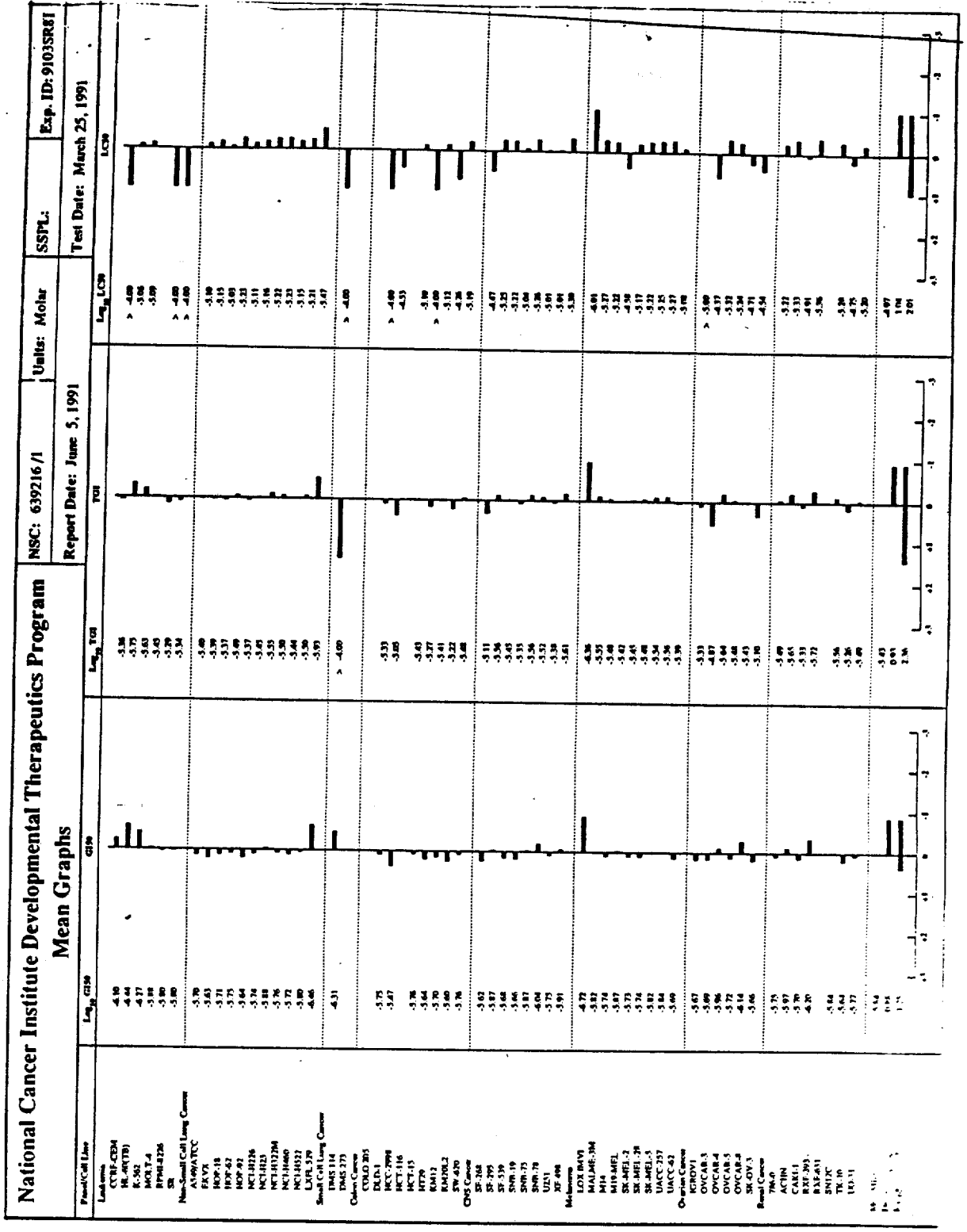
TABLE II (See EXAMPLE 13)

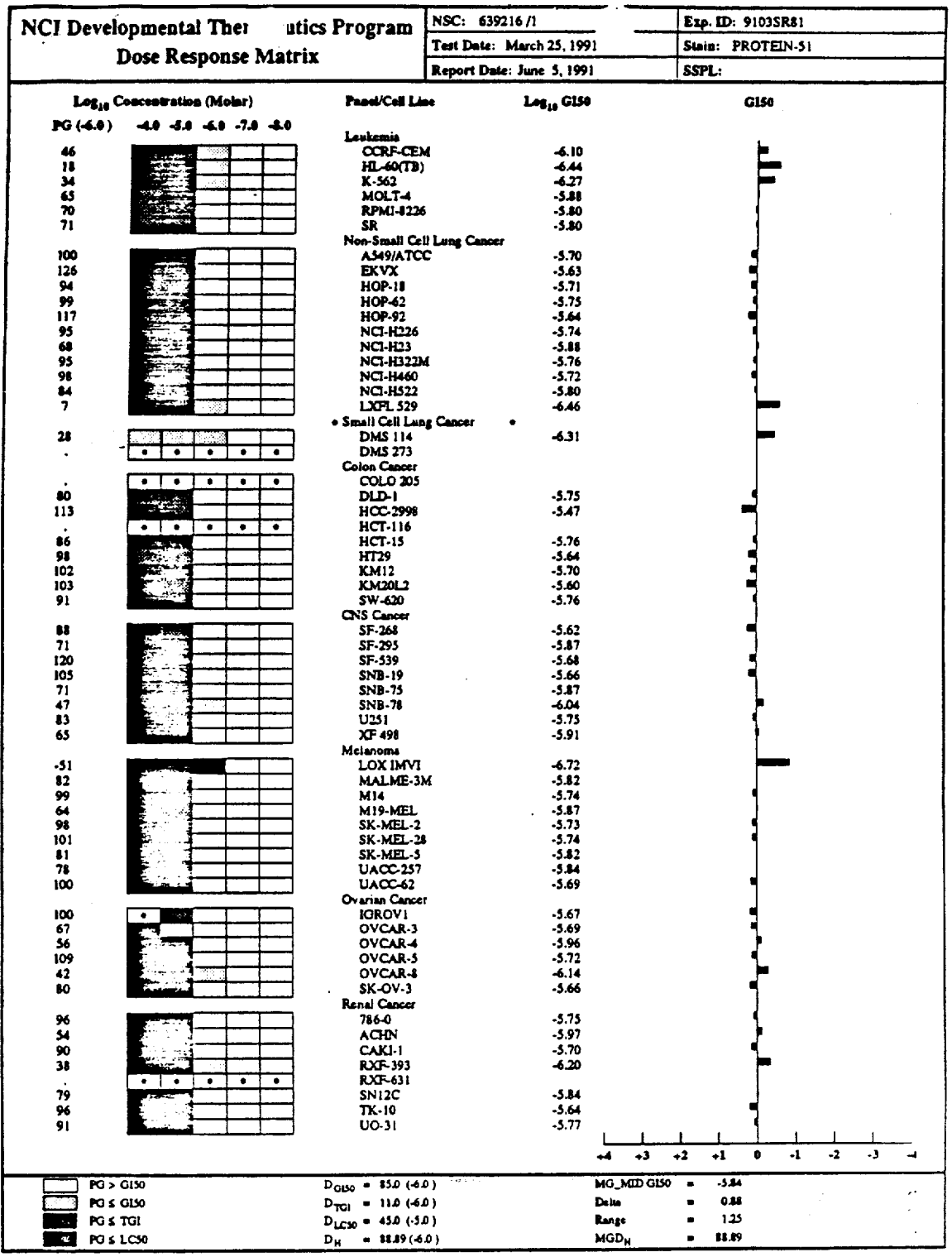
TABLE III (See EXAMPLE 13)

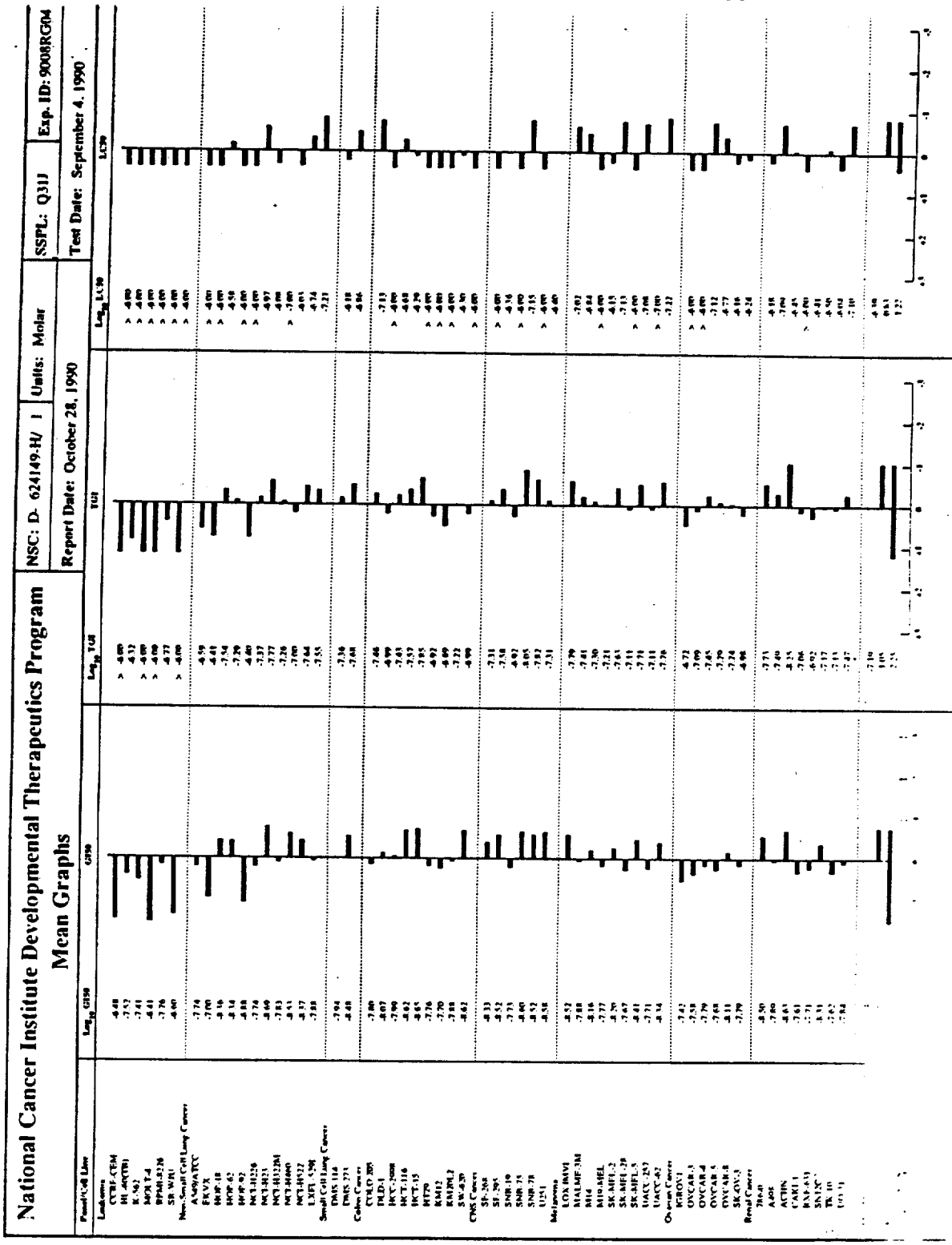
TABLE IV (See EXAMPLE 14)

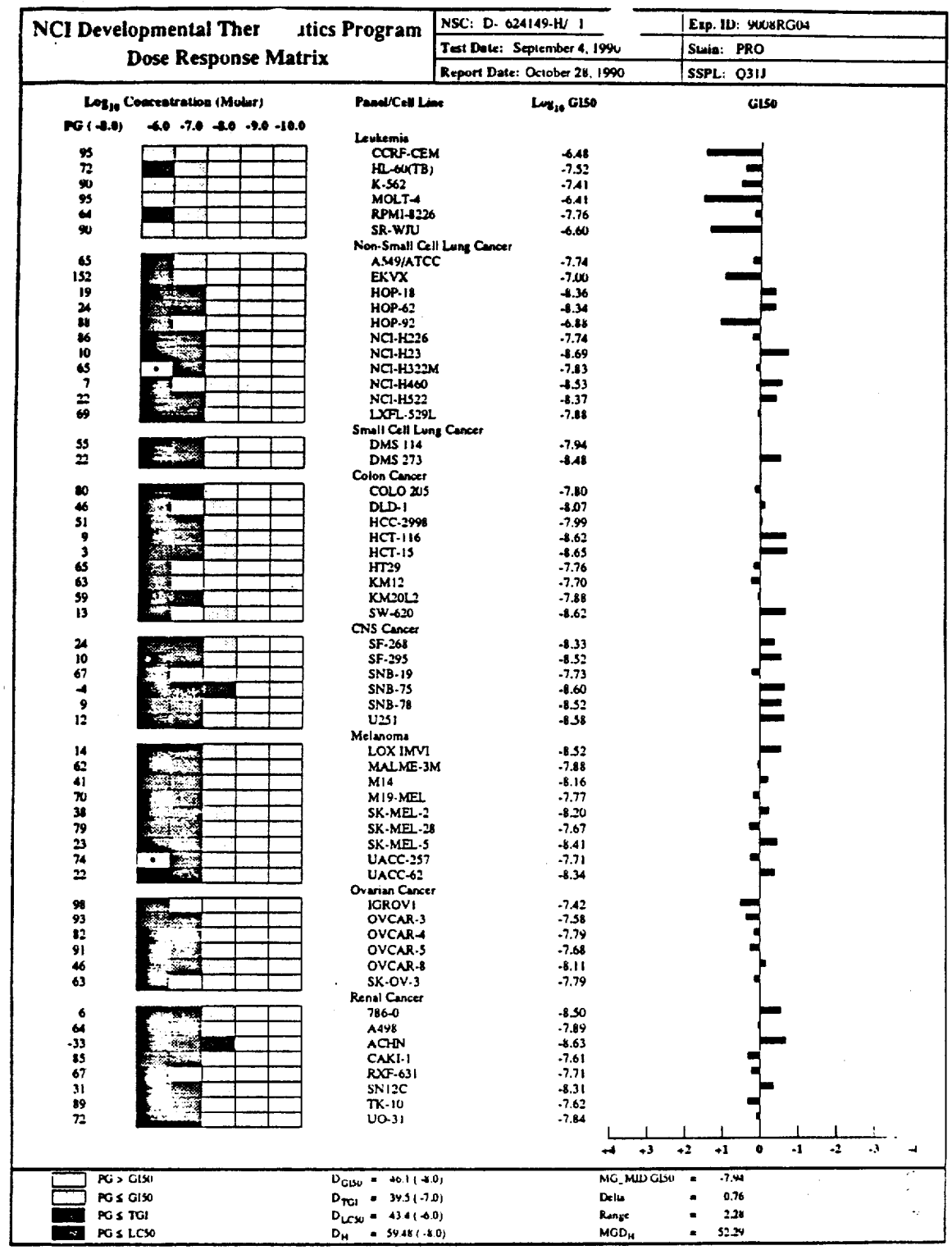
TABLE V (See EXAMPLE 14)

TABLE VI (See EXAMPLE 15)

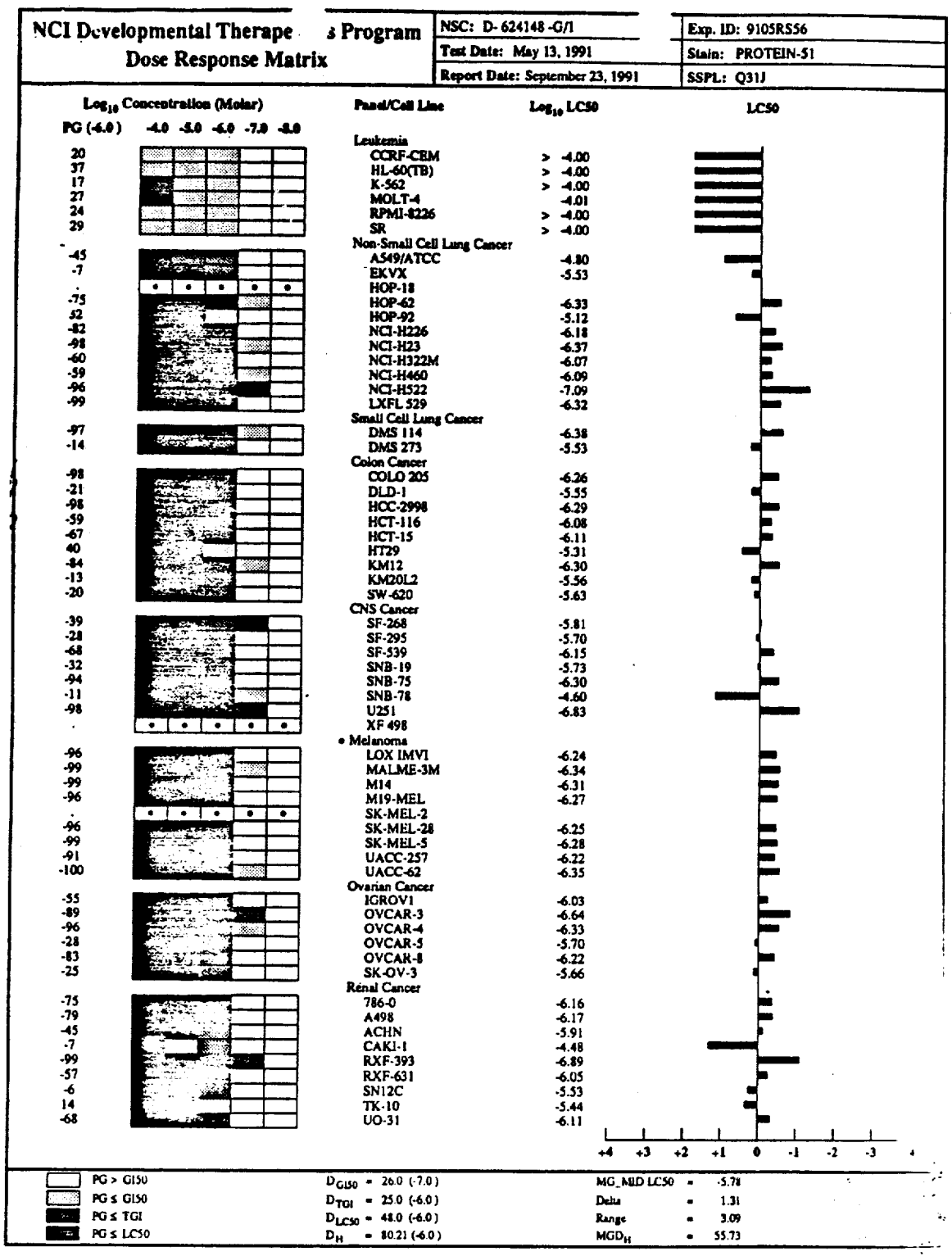
TABLE VII (See EXAMPLE 15)

TABLE VIII (See EXAMPLE 16)

| NCI Developmental Therapeutics Program Dose Response Matrix | NSC: 639215/1 | Exp. ID: 9103SR81 |
|---|---|---|
| | Test Date: March 25, 1991 | Si-in: PROTEIN-51 |
| | Report Date: June 5, 1991 | SSPL: |

| Log₁₀ Concentration | Panel/Cell Line | Log₁₀ GI50 |
|---|---|---|
| PG (-5.0) -4.0 -5.0 -6.0 -7.0 -8.0 | | |
| | Leukemia | |
| . | CCRF-CEM | < -8.00 |
| -56 | HL-60(TB) | < -8.00 |
| . | K-562 | < -8.00 |
| | MOLT-4 | -6.91 |
| -41 | RPMI-8226 | < -8.00 |
| -21 | SR | -7.51 |
| | Non-Small Cell Lung Cancer | |
| -65 | A549/ATCC | -7.09 |
| -95 | EKVX | -7.63 |
| -100 | HOP-18 | -7.36 |
| -99 | HOP-62 | -7.64 |
| -41 | HOP-92 | -6.55 |
| -74 | NCI-H226 | -6.76 |
| -68 | NCI-H23 | < -8.00 |
| -98 | NCI-H322M | -6.95 |
| -48 | NCI-H460 | -7.64 |
| -87 | NCI-H522 | < -8.00 |
| -100 | LXFL 529 | < -8.00 |
| | Small Cell Lung Cancer | |
| 10 | DMS 114 | -7.77 |
| . | DMS 273 | |
| | Colon Cancer | |
| . | COLO 205 | |
| -18 | DLD-1 | -7.92 |
| -98 | HCC-2998 | -7.63 |
| . | HCT-116 | |
| -74 | HCT-15 | -7.65 |
| -73 | HT29 | -7.50 |
| -95 | KM12 | -7.70 |
| -61 | KM20L2 | -7.52 |
| -92 | SW-620 | < -8.00 |
| | CNS Cancer | |
| -52 | SF-268 | -7.63 |
| -89 | SF-295 | < -8.00 |
| -99 | SF-539 | -7.68 |
| -100 | SNB-19 | -7.43 |
| -98 | SNB-75 | -7.46 |
| -55 | SNB-78 | < -8.00 |
| -100 | U251 | -7.40 |
| -95 | XF 498 | -7.70 |
| | Melanoma | |
| -98 | LOX IMVI | -7.89 |
| -93 | MALME-3M | -6.84 |
| -93 | M14 | < -8.00 |
| -53 | M19-MEL | -6.66 |
| -90 | SK-MEL-2 | -7.32 |
| -98 | SK-MEL-28 | -7.41 |
| -89 | SK-MEL-5 | -7.69 |
| -60 | UACC-257 | -6.91 |
| -71 | UACC-62 | -6.84 |
| | Ovarian Cancer | |
| -84 | IGROV1 | -7.47 |
| -4 | OVCAR-3 | < -7.00 |
| -99 | OVCAR-4 | < -8.00 |
| -99 | OVCAR-5 | -7.56 |
| -82 | OVCAR-8 | -7.30 |
| -98 | SK-OV-3 | -6.94 |
| | Renal Cancer | |
| -100 | 786-0 | -7.96 |
| -99 | ACHN | < -8.00 |
| | CAKI-1 | -7.55 |
| -99 | RXF-393 | < -8.00 |
| | RXF-631 | |
| -99 | SN12C | -7.51 |
| -99 | TK-10 | -7.15 |
| -99 | UO-31 | -7.68 |

| | |
|---|---|
| PG > GI50 | $D_{GI50}$ = 46.0 (-8.0) |
| PG ≤ GI50 | $D_{TGI}$ = 26.0 (-7.0) |
| PG ≤ TGI | $D_{LC50}$ = 30.0 (-6.0) |
| PG ≤ LC50 | $D_H$ = 80.00 (-5.0) |

| | |
|---|---|
| MG_MID GI50 | -7.54 |
| Delta | 0.46 |
| Range | 1.45 |
| MGD_H | 39.29 |

TABLE IX (See EXAMPLE 16)

From the foregoing it becomes readily apparent that a new and useful cell growth inhibitory factor and new and useful cytostatic preparations have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto.

Accordingly, what is claimed is:

1. A pharmaceutical preparation for treating colon cancer comprising a pharmaceutically acceptable carrier and a tumor-inhibiting amount of an azamitosene.

2. A preparation according to claim 1 in which said azamitosenes have the structural formula:

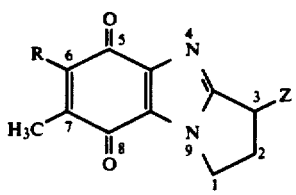

wherein:
R is

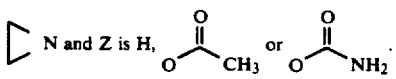

3. A pharmaceutical preparation according to claim 1 in which the azamitosene is selected from the group consisting of 6-(N-Aziridinyl)-7-methyl-2, 3-dihydro-1H-pyrrolo benzimidazole-5,8-dione-3-acetate, and 6-(N-Aziridinyl)-7-methyl-2, 3-dihydro-1H-pyrrolo benzimidazole-5, 8-dione-3-carbamate.

4. A pharmaceutical preparation for treating a neoplastic disease selected from the group consisting of colon cancer, ovarian cancer, and myeloma comprising a pharmaceutically acceptably carrier and a tumor-inhibiting amount of a compound selected from the group consisting azamitosenes having the structural formula:

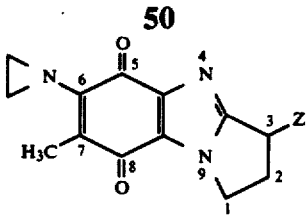

wherein Z is selected from the group consisting of

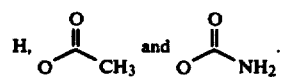

5. A method of treating a host afflicted with a neoplastic disease selected from the group consisting of colon cancer, ovarian cancer, and myeloma, comprising administering to said host an effective amount of a compound selected from the group consisting of:

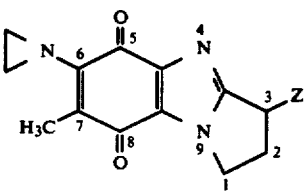

wherein Z is selected from the group consisting of

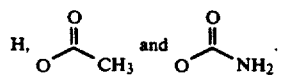

6. A method according to claim 5 in which said substance is administered intravenously, at a dosage level of from 0.1 up to about 20 mg per kilogram of host body weight.

7. A method according to claim 5 in which said substance is administered intravenously, at a dosage level of from 1 up to about 50 mg per kilogram of host body weight.

8. A method according to claim 5 in which said substance is administered orally, at a dosage level of from 5 up to about 100 mg per kilogram of host body weight.

9. A method according to claim 5 in which said effective amount comprises from about 1 up to about 4 g per kilogram of host body weight.

* * * * *